United States Patent
Binning et al.

(10) Patent No.: US 9,215,863 B2
(45) Date of Patent: *Dec. 22, 2015

(54) METHOD OF EVALUATING PLANT PROTECTION

(75) Inventors: Rachel R. Binning, Clive, IA (US); Fu-Chih Cheng, Overland Park, KS (US); Bo Hong, Ankeny, IA (US); Stephen A. Lefko, River Forest, IL (US); Timothy M. Nowatzki, Granger, IA (US); Bruce H. Stanley, Wilmington, DE (US); Stephen D. Thompson, Urbandale, IA (US); Deanne L. Wright, Madrid, IA (US)

(73) Assignees: Pioneer Hi-Bred International, Inc., Johnston, IA (US); E.I. Du Pont de Nemours and Company, Wilmington, DE (US)

( * ) Notice: Subject to any disclaimer, the term of this patent is extended or adjusted under 35 U.S.C. 154(b) by 412 days.

This patent is subject to a terminal disclaimer.

(21) Appl. No.: 13/072,320

(22) Filed: Mar. 25, 2011

(65) Prior Publication Data

US 2011/0236319 A1    Sep. 29, 2011

Related U.S. Application Data

(63) Continuation-in-part of application No. 11/272,992, filed on Nov. 14, 2005, now Pat. No. 7,939,707.

(60) Provisional application No. 60/627,599, filed on Nov. 12, 2004.

(51) Int. Cl.
*A01H 1/04* (2006.01)
*A01K 67/033* (2006.01)
*A01N 25/00* (2006.01)

(52) U.S. Cl.
CPC .............. *A01K 67/033* (2013.01); *A01N 25/00* (2013.01)

(58) Field of Classification Search
CPC ........ A01K 67/033; A01N 25/00; A01H 1/04
USPC ................................. 800/265, 275
See application file for complete search history.

(56) References Cited

U.S. PATENT DOCUMENTS 5,763,245 A     6/1998  Greenplate et al.
7,939,707 B2*   5/2011  Lefko et al. ................... 800/265

FOREIGN PATENT DOCUMENTS

WO    WO 00/04049 A1    1/2000

OTHER PUBLICATIONS

Moellenbeck et al (Nature Biotechnology 19: 668-672, 2001).*
Matthews et al (J. Invertebrate Pathology 80: 73-80, 2002).*
Singsit et al (Transgenic Research 6: 169-176, 1997).*
Godin et al (J. Econ. Entomology 95(6): 1308-1313, 2002).*
Hammack et al (Field and Forage Crops 96(4): 1153-1159, 2003).*
Fitches et al (J. Insect Physiol. vol. 43, No. 8, pp. 727-739, 1997).*
Moellenbeck et al. Nature Biotechnology 19: 668-672, 2001.*
Matthews et al. J. Invertebrate Pathology 80: 73-80, 2002.*
Singsit et al. Transgenic Research 6: 169-176, 1997.*
Godin et al. J. Econ. Entomology 95(6): 1308-1313, 2002.*
Fitches et al. J. Insect Physiol. vol. 43, No. 8, pp. 727-739, 1997.*
Clark et al.; "Plant-Insect Interactions—Comparison of Nonmaize Hosts to Support Western Corn Rootwork (Coleoptera: Chrysomelidae) Larval Biology"; *Environmental Entomology*; Jun. 2004; pp. 681-689; vol. 33, No. 3, (XP008061316).
Nowatzki, et al.; "Validation of a Novel Resistance Monitoring Technique for Corn Rootworm (Coleoptera: Chrysomelidae) and Event DAS-59122-7 Maize"; *J. Appl. Entomol.*; 2008; pp. 177-188; vol. 132.
Godin et al., "Head Capsule Width as an Instar Indicator for Larvae of the Cranberry Fruitworm (Lepidoptera: Pyralidae) in Southeastern New Brunswick," *J. Econ. Entomol.*, 2002, vol. 95(6), pp. 1308-1313.
Goldson et al., "Seasonal Variation in Larval-Instar Head-Capsule Sizes of Argentine Stem Weevil, *Listronotus bonariensis* (Kuschel)(coleopteran: Curculionidae)," *Aust. J. Entamol.*, 2001, vol. 40, pp. 371-375.
Hammack et al., "Larval Sampling and Instar Determination in Field Populations of Northern and Western Corn Rootworm (Coleoptera: Chrysomelidae)," *J. Econ. Entomol.*, 2003, vol. 96(4), pp. 1153-1159.
Hochuli et al., "Analysis of Endoparasitoid-Released Proteins and Their Effects on Host Development in the System *Chelonus inanitus* (Braconidae)—*Spodoptera littoralis* (Noctuidae)," *J. Insect Physiol.*, 1999, vol. 45, pp. 823-833.
Pszczolkowski et al., "Feeding and Development of *Cydia pomonella* ( Lepidoptera: Tortricidae) Larvae on Apple Leaves," *Ann. Entomol. Soc.*, 2002, vol. 95(5), pp. 603-607.

(Continued)

*Primary Examiner* — Keith O. Robinson
(74) *Attorney, Agent, or Firm* — Pioneer Hi-Bred Int'l

(57) ABSTRACT

A method is provided for evaluating a protected plant having a protection mechanism. A population of immature insects (i.e., larvae or nymphs) belonging to an insect species having a plurality of instars is first exposed to the protected plant such that the protected plant is at least contacted thereby. The insect exposure extends for a selected time period corresponding to a sublethal exposure of the insect population to the protected plant. The exposure of the insect population to the protected plant is then halted following the selected time period and insects collected. A physical characteristic of at least some collected insects is measured. The measured physical characteristics are then statistically analyzed so as to determine an efficacy of the protection mechanism of the protected plant with respect to the insect population. Associated methods are also provided.

20 Claims, 10 Drawing Sheets

(56) References Cited

OTHER PUBLICATIONS

Ramachandran et al., "Survival, Development, and Oviposition of Resistant Diamondback Moth (Lepidoptera: Plutellidae) on Transgenic Canola Producing a *Bacillus thruingiensis* Toxin," *J. Econ. Entomol.*, 1998, vol. 91(6), pp. 1239-1244.

Verdinelli et al., "Development and Feeding Efficiency of *Malacosoma neustrium* Larvae Reared with *Quercus* spp. Leaves," *Ann. Appl. Biol.*, 2003, vol. 143, pp. 161-167.

Eubanks, M.W., "Experimental Investigation of a Gene for Resistance to Corn Rootworm, *Diabrotica* spp," *American Journal of Botany*, 1997, p. 116, vol. 84(6 Suppl.).

Fitches et al., "Effects of Snowdrop Lectin (GNA) Delivered Via Artifical Diet and Transgenic Plants on the Development of Tomato Moth (*Lacanobia oleracea*) Larvae in Laboratory and Glasshouse Trials," *J. Insect Physiol.*, 1997, pp. 727-739, vol. 43(8).

Wilson et al.; "Host Suitability of Nonmaize Agroecosystem Grasses for the Western Corn Rootworm Coleoptera: Chrysomelidae)", *Environmental Entomology*, Aug. 2004, vol. 33, No. 4, pp. 1102-1108.

Moellenbeck et al., Nature Biotechnology, 2001, vol. 19, pp. 668-672.

Singsit et al., 1997, Transgenic Research, 1997, vol. 6, pp. 169-176.

Matthews et al., J. Invertebrate Pathology, 2002, vol. 80, pp. 73-80.

Examination Report for European Patent Application No. 05 825 732.0 dated Aug. 22, 2007.

\* cited by examiner

METHOD OF EVALUATING PLANT PROTECTION

CROSS-REFERENCE TO RELATED APPLICATIONS

This application is a continuation-in-part of U.S. application Ser. No. 11/272,992, filed on Nov. 14, 2005 now U.S. Pat. No. 7939707, which claims the benefit of U.S. Provisional Application No. 60/627,599, filed Nov. 12, 2004, each of which is hereby incorporated herein in its entirety by reference.

BACKGROUND OF THE INVENTION

1. Field of the Invention

The present invention relates to methods of evaluating plant protection and, more particularly, to a method of evaluating the efficacy of a plant protection mechanism or other plant characteristic for resistance against an insect.

2. Description of Related Art

Many insect pests of crop plants cause damage which can be difficult to measure precisely. Because this damage can be difficult to measure, it can also be difficult to determine whether a particular plant protection mechanism is effective in reducing damage from insect pests.

For example, the western and northern corn rootworm, *Diabrotica virgifera virgifera* and *D. barberi*, respectively, are perennial insect pests of corn across most of the Corn Belt. Both species are univoltine and overwinter as eggs in the soil, typically of cornfields. The larvae of such pests are often the most damaging insect stage. Larval feeding on the roots reduces crop yield by limiting transport of water and nutrients from the soil and increasing plant susceptibility to lodging.

Historically, plant protection mechanisms used against these pests have included crop rotation and/or synthetic insecticides applied to the soil at planting time. The protection provided by insecticides against corn rootworm larvae has traditionally been evaluated subjectively in field plots by visually scoring the amount of root damage relative to an unprotected control. Root damage ratings have generally been adopted as the standard evaluation tool for the efficacy of plant protection mechanisms against corn rootworm because root ratings provide direct evidence of the measure of protection. However, it has been inefficient or impractical to relate the direct effects of a plant protection mechanism on the insects to the root injury expected in a field setting. Although root ratings do provide a useful tool for categorizing the efficacy of protection mechanisms against corn rootworm, such methods may lack statistical validity, and study results may be difficult to interpret because of, for example, variability associated with interactions between the insect, the protection mechanism, maize genetics, and the environment.

One example of a plant protection mechanism is a transgene (such as, for example, a polynucleotide encoding an insecticidal protein) that is incorporated into a plant so as to, for example, protect a maize plant from corn rootworm. Such a plant protection mechanism may have unique biological, physiological, and/or regulatory characteristics that may make evaluation of its efficacy relatively more complex with respect to, for example, other plant protection mechanisms. By "transgene" is intended a gene or polynucleotide that has been introduced into the plant genome by human intervention, such as by transformation and/or by breeding.

One of the first issues in the development process for such plant protection mechanisms is identifying insecticidal proteins with suitable bioactivity properties against the target pest. Historically, evaluation of such proteins was accomplished using an artificial diet bioassay for the insects wherein the diet was treated with purified insecticidal protein and the evaluation was based on the number of insects that died during the bioassay. However, using the death of the insect as a measure of efficacy has several drawbacks. First, death is a relatively crude measurement of the impact of a particular treatment. Also, death may be due to factors other than the insecticidal protein. With soil-inhabiting insects like corn rootworm, diet contamination is an important factor that can limit the interpretation and precision of bioassay results. Additionally, the cost of such assays is typically high due to the need for purified insecticidal protein. Further, protein bioactivity observed in a diet bioassay may not necessarily correlate to efficacy of a protection mechanism in plants expressing the insecticidal protein under field conditions.

Another important step in the development process of a plant protection mechanism which is a transgene is that the efficacy of several independent transformation events are typically evaluated. A transformation event results from the process by which a transgene is inserted into the plant genome, and transformation events typically vary in their expression levels and consequently in the efficacy of a plant protection mechanism provided thereby. Accordingly, it is standard in the art to evaluate the efficacy of at least several independent transformation events by evaluating the trait in plants that contain a transformation event.

In such evaluations of efficacy for traits intended to provide protection against corn rootworm, root damage ratings typically are used to identify events that may have levels of efficacy suitable for commercial use. However, measurements of root damage have several drawbacks, including a requirement for large sample sizes in order to increase precision. The large sample sizes required are often difficult to obtain from a limited number of transgenic plants. There is also inherent variability associated with the root rating measurements, and these factors both act to limit predictability when attempting to discriminate subtle differences in efficacy between transformation events. Thus, for example, it would be helpful to have a relatively sensitive bioassay in order to distinguish and characterize differences among: transgenic plants comprising different insecticidal proteins; differences among transformation events using the same trait; differences between the same event expressed across a number of genetic backgrounds; and interactions among stacked transgenic events that produce changes in efficacy.

Another factor that may add complexity to the trait development process includes enhanced regulatory scrutiny of transgenic crops. Prior to commercialization, the amount of data that can be collected in field studies can be limited by strictly regulated experimental use permits and limited quantities of experimental seed. The regulatory approval process also often requires additional information related to insect resistance monitoring and management and the potential for adverse environmental effects. Collecting such data requires specialized tools and high-precision protocols.

One of the additional regulatory requirements unique to transgenic plant protection mechanisms in the United States is proactive annual monitoring for insect resistance to detect early warning signs indicating resistance development in the field. Detection of resistant insects in these monitoring programs depends, for example, on the level of pest pressure, frequency of resistant individuals, number of samples, and sensitivity of the detection technique. Analytical techniques for resistance monitoring have been developed for Lepidopteran pests and transgenic plants that protect against them. However, new monitoring tools for transgenic plants that protect against other insects, such as soil-inhabiting insects (e.g., corn rootworm) are needed, particularly in view of differing insect life cycles and different sensitivities to insecticidal agents.

Thus, there exists a need for a method of evaluating the efficacy of plant protection mechanisms that minimizes or eliminates the described limitations that may have been encountered with previous studies. Such a method should preferably minimize or eliminate subjective factors and/or the effects of the natural environment and contamination. Such a method should have the predictive power or sensitivity to detect minute or otherwise subtle differences in efficacy while overcoming the limitation of experimental material that is inherent in the transgenic seed product development process. Such a method should be suited to the biology of the target pest and be sufficiently flexible to allow research and regulatory questions to be efficiently addressed while minimizing concerns related to the permits that may be necessary to conduct such efficacy studies.

BRIEF SUMMARY OF THE INVENTION

The above and other needs are met by the present invention which, in one embodiment, provides a method of evaluating a protected plant. A population of immature insects (i.e., larvae or nymphs) belonging to an insect species having a plurality of instars is first exposed to the protected plant such that there is insect contact with and/or ingestion of (at least contact with) the protection mechanism of the protected plant. The exposure extends for a selected time period corresponding to a sublethal exposure of the insect population to the protected plant. The exposure of the insect population to the protected plant is then halted following the selected time period and the immature insects are collected. The total count of recovered insects may be statistically analyzed, by treatment, as one measure of efficacy of the protection mechanism. A physical characteristic of each insect is also measured. In some embodiments, the insect population is then sorted into instars based on the measured physical characteristic. In some embodiments, the distribution of the measured physical characteristics is statistically analyzed as a measure of an efficacy of the protection mechanism of the protected plant with respect to the insect population. In some embodiments, the distribution of the measured physical characteristics across the instars is statistically analyzed as another measure of an efficacy of the protection mechanism of the protected plant with respect to the insect population.

In various embodiments, the statistical analysis of the total insect count and the measured physical characteristics may include evaluation of, for example, a difference in efficacy between plant protection mechanisms, a difference in efficacy between populations of the same insect species, a difference in efficacy between at least two specimens of the protected plant each prepared with the same protection mechanism, a difference in efficacy between a transgenic plant prepared with a single trait versus a transgenic plant prepared with more than one trait, a difference in efficacy of the protection mechanism of the protected plant between at least two insect species, a difference in efficacy of the protection mechanism of the protected plant for at least two insect species between at least two specimens of the protected plant each prepared with the protection mechanism, and a difference in efficacy of the protection mechanism between insect populations each with different levels of exposure (i.e., resistance) to a protection mechanism.

Embodiments of the present invention provide significant advantages as further described herein.

BRIEF DESCRIPTION OF THE DRAWINGS

Figure 1:
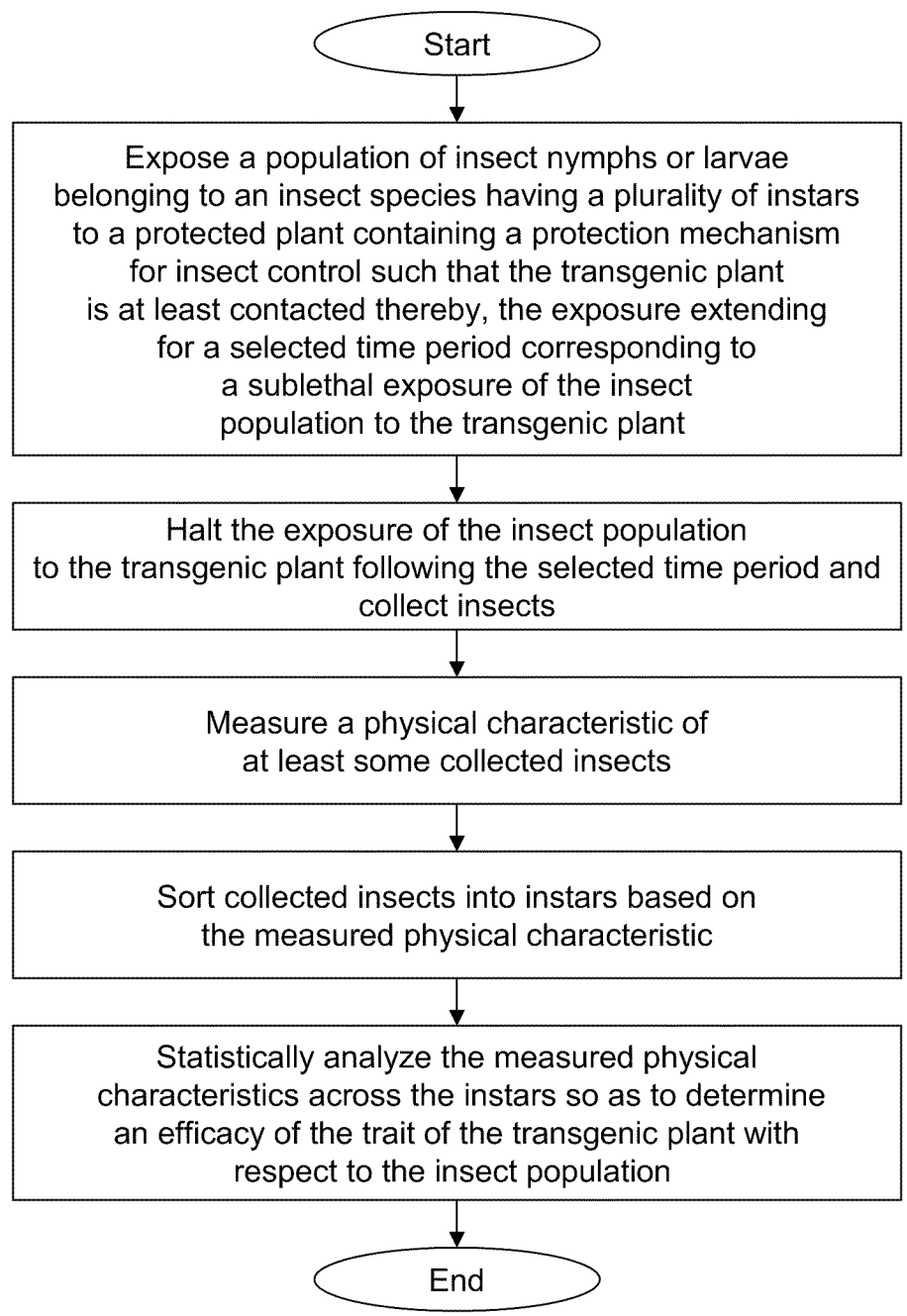
Figure 2:
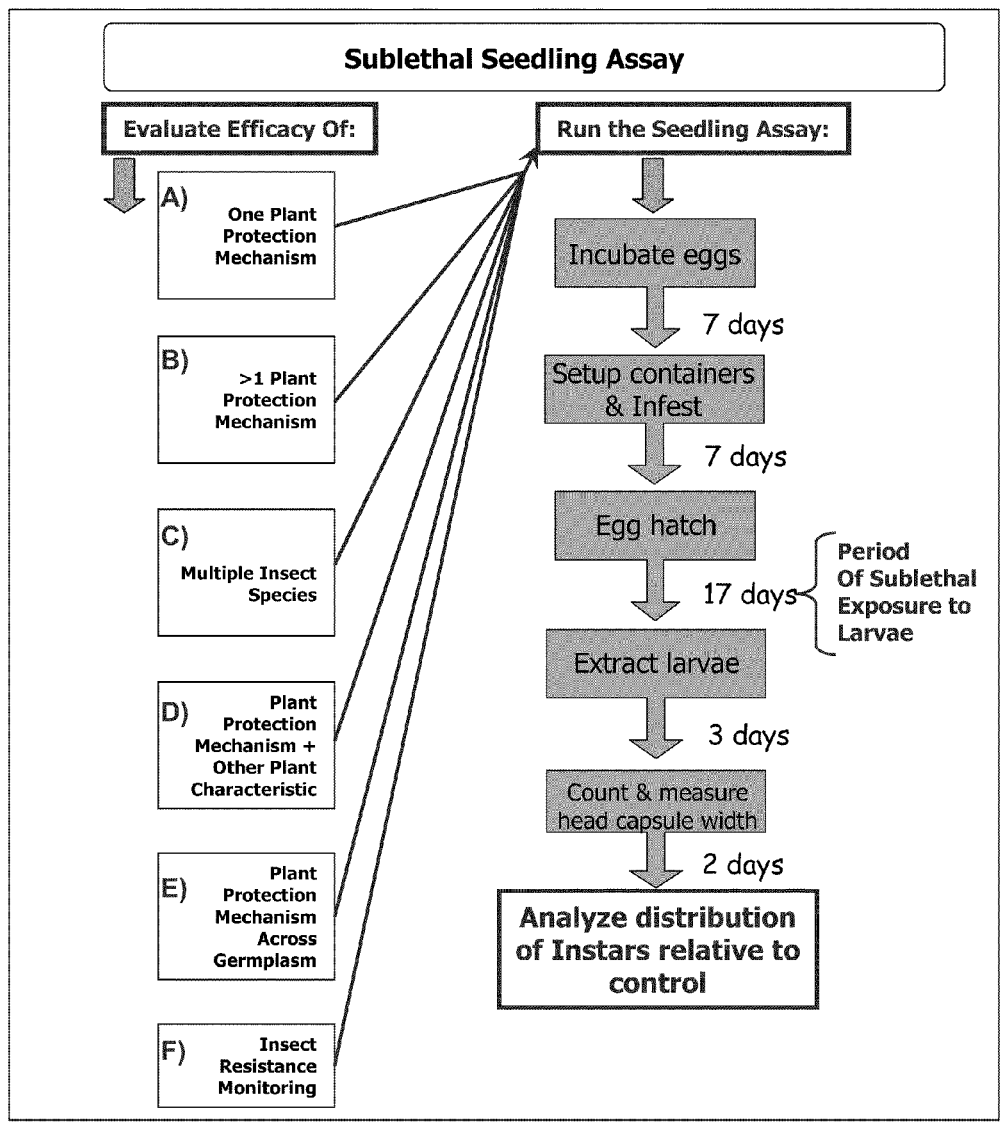
Figure 3:
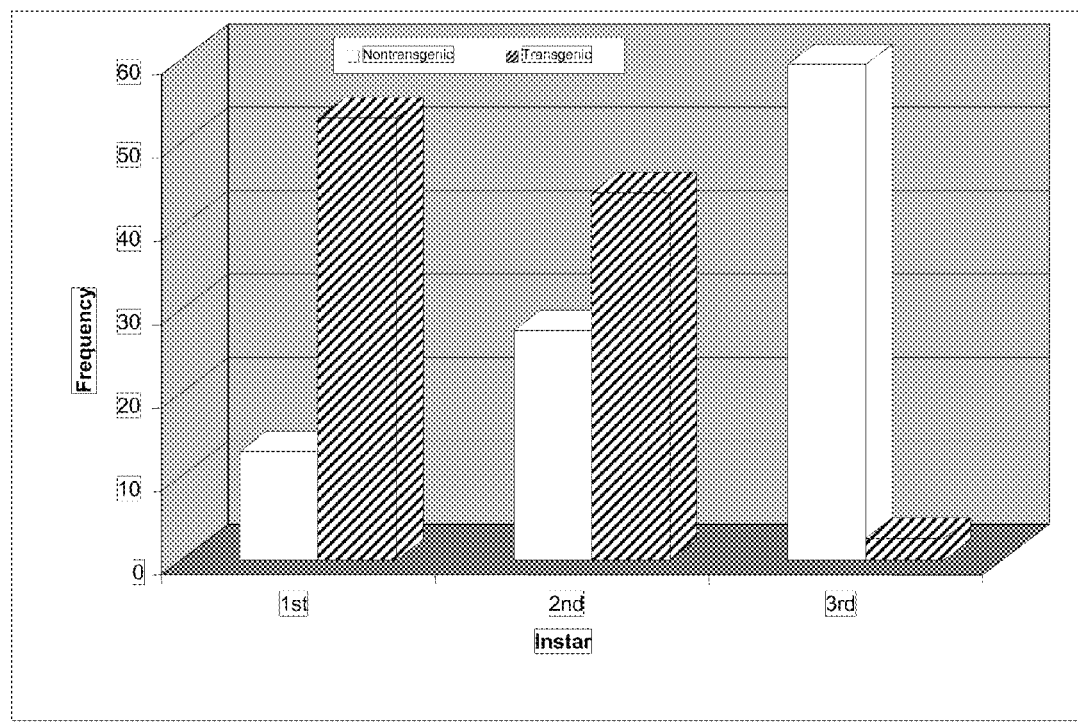
Figure 4A:
Figure 4B:
Figure 5:
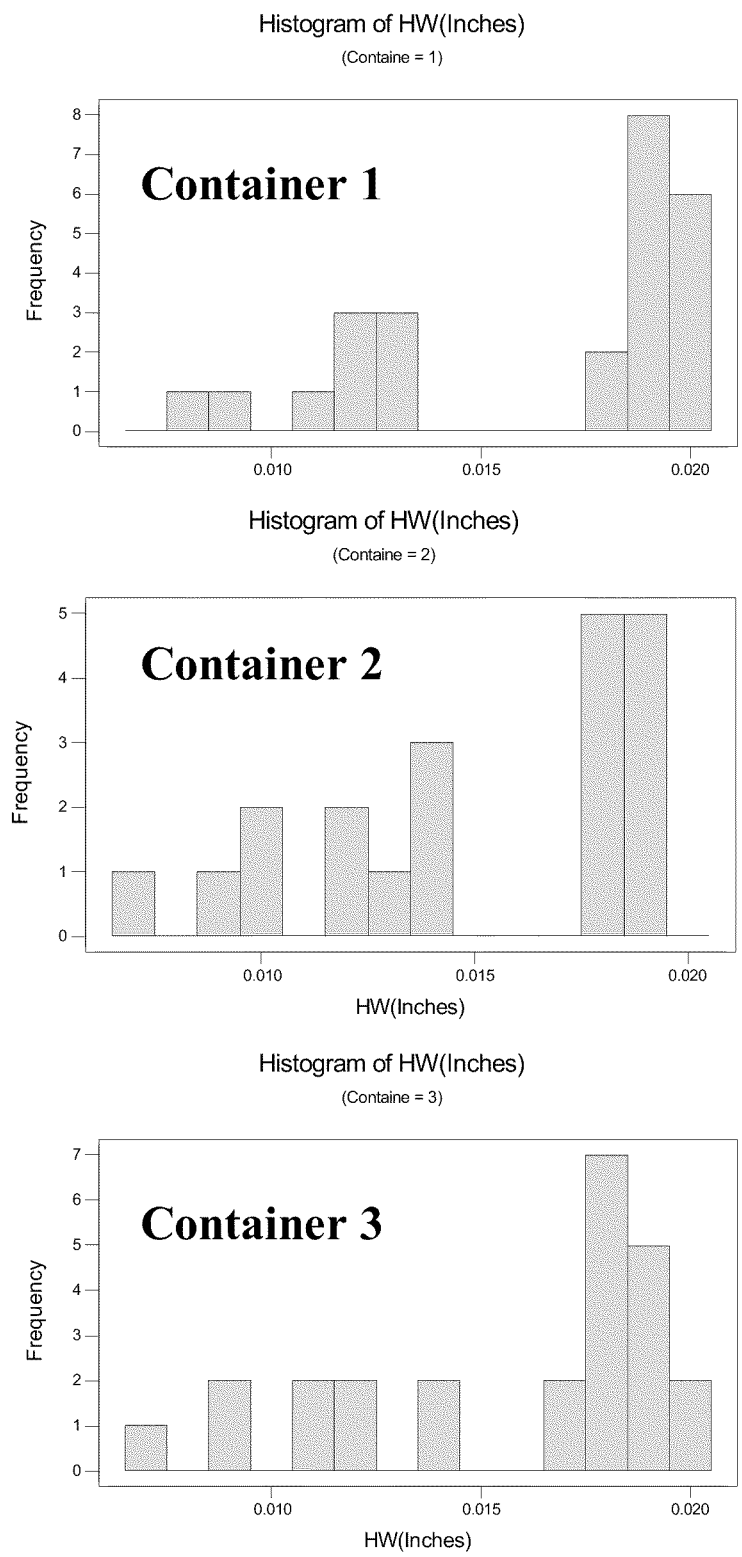
Figure 6:
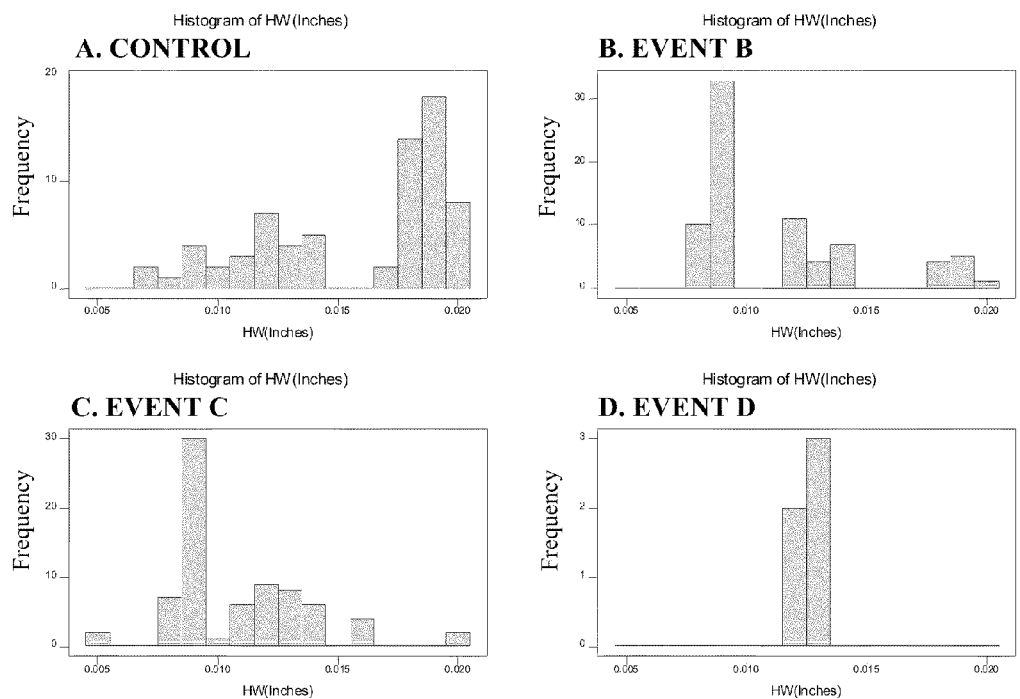
Figure 7:
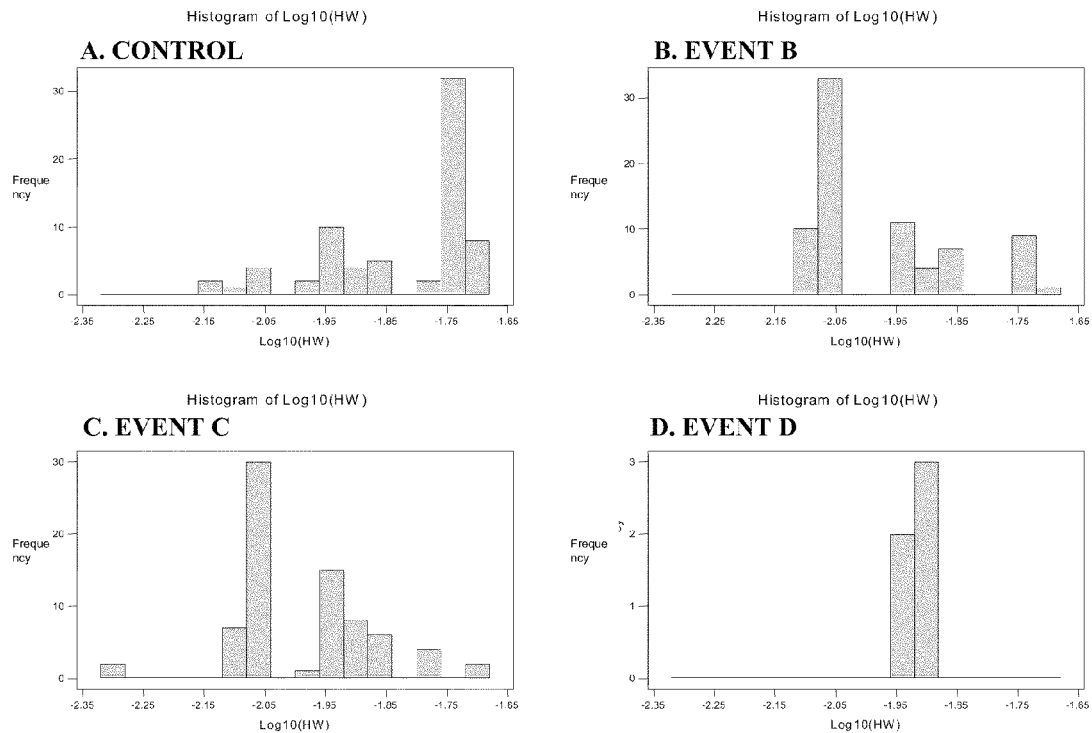
Figure 8:
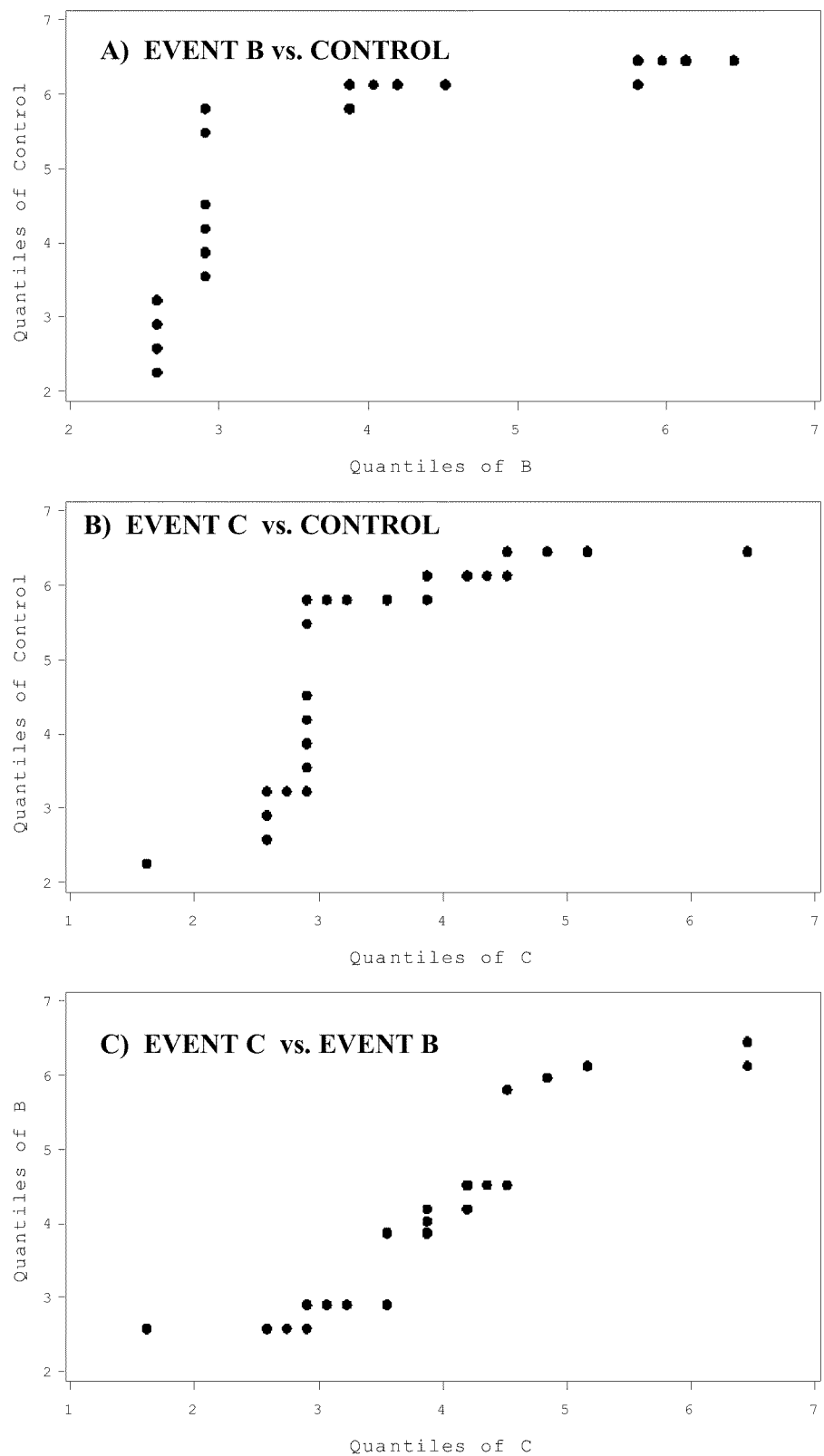
Figure 9:
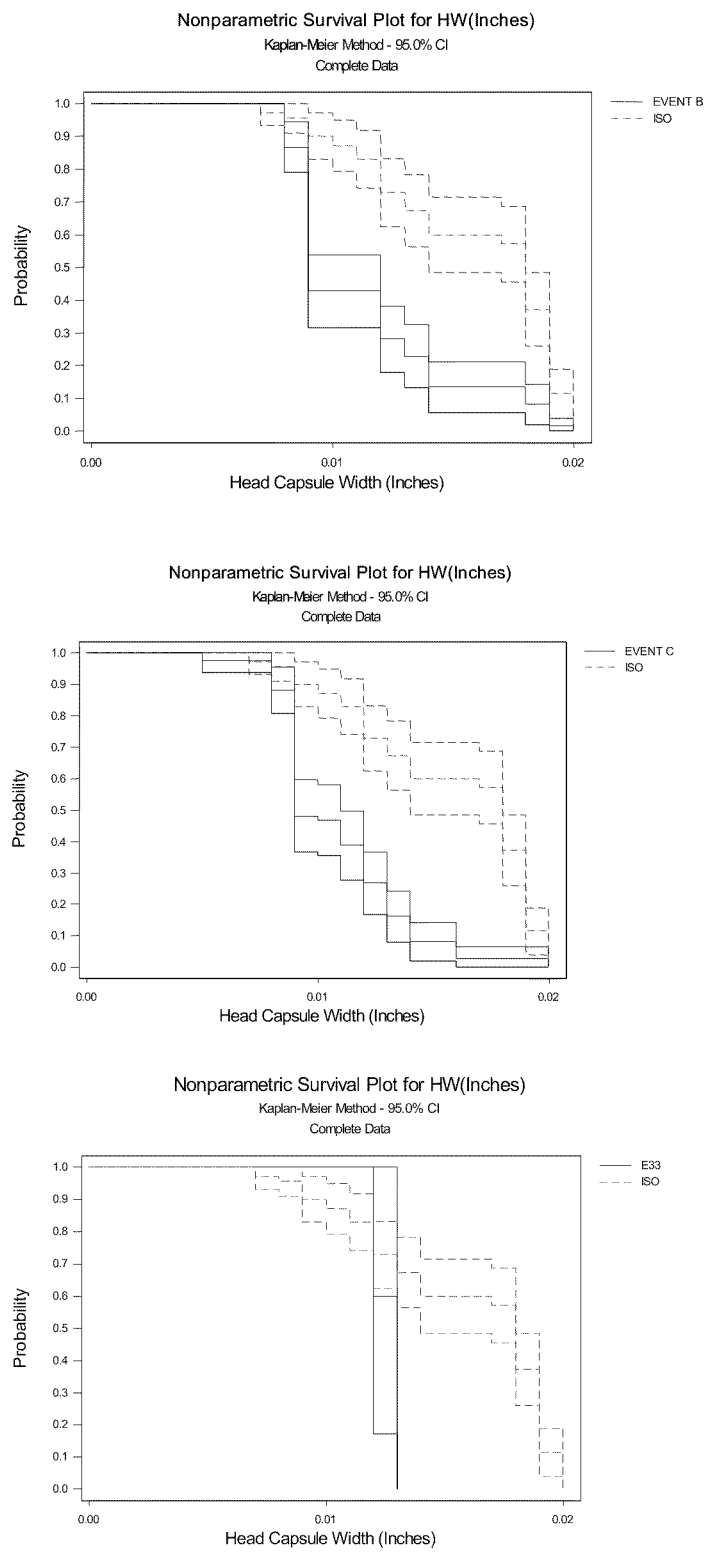
Figure 10:
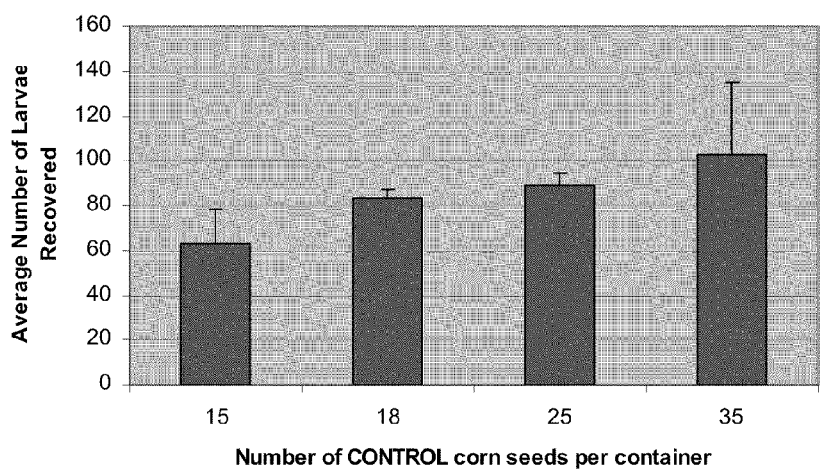

Having thus described the invention in general terms, reference will now be made to the accompanying drawings, which are not necessarily drawn to scale, and wherein:

FIG. 1 schematically illustrates a method of evaluating a protected plant having a plant protection mechanism, according to one embodiment of the present invention;

FIG. 2 schematically illustrates a sublethal seedling exposure assay methodology according to one embodiment of the present invention, as applied to a corn rootworm, capable of, for example, evaluating efficacy, monitoring for insect resistance, and characterizing dosage of a protection mechanism. More particularly, FIG. 2 illustrates a corn rootworm sublethal seedling exposure assay methodology for evaluating efficacy of rootworm plant protection mechanisms, and monitoring for changes in rootworm population susceptibility (resistance) to the protection mechanism, wherein such an assay is capable of evaluating efficacy against an insect between:

(A) One plant protection mechanism vs. an unprotected plant, wherein the distribution of instars associated with the protected plant may be shifted toward earlier instars compared to the unprotected plant, which may have a distribution shifted toward later instars;

(B) Multiple plant protection mechanisms (each in a separate plant) vs. an unprotected plant, wherein the protection mechanism providing the greatest efficacy may have a distribution of instars with the greatest shift toward earlier instars;

(C) One insect species exposed to a plant protection mechanism (i.e., species A) vs. other species exposed to the same protection mechanism (i.e., species B, species C), wherein a distribution of instars for species A shifted further toward later instars than the respective distributions for species B and C is indicative of lower efficacy against species A compared to species B and C;

(D) A plant protection mechanism which is a transgenic trait vs. the same plant protection mechanism plus one additional protection mechanism (i.e., an insecticidal seed treatment), wherein a distribution of instars shifted toward earlier instars for the trait+seed treatment protection mechanism is indicative of a synergistic efficacy compared to the transgenic trait alone;

(E) One plant protection mechanism applied to a range of different plant germplasm lines (i.e., a transgenic trait in hybrid 1, hybrid 2 & hybrid 3), wherein a distribution of instars that is the same for hybrid 1 and 2, but is shifted toward later instars for hybrid 3, is indicative of a lesser efficacy of the trait functioning in hybrid 3; and (F) Insect populations that have developed resistance to plant protection mechanisms will have a distribution shifted toward later instars compared to an insect population known to be susceptible (e.g., determined baseline susceptibility prior to any exposure);

FIG. 3 schematically illustrates an exemplary distribution of a physical characteristic measurement for an insect population in accordance with one embodiment of the present invention. The distribution was determined for larval head capsule width of corn rootworm larvae after exposure to non-protected and protected corn in a seedling assay, wherein the shift in development toward 1st and 2nd instars on the protected exposure, relative to development on an unprotected control, indicates, for example, efficacy of a plant protection mechanism (here, a transgene);

FIG. 4A depicts an example of a scanned image of collected insects used to calculate larval body size;

FIG. 4B depicts an example of isolation of the larvae from a background image as performed by image analysis software;

FIG. 5 depicts Diagram 1: Distribution of Head Capsule Widths in Each Container for the Reference (CONTROL);

FIG. 6 depicts Diagram 2: Head Capsule Width Distributions for Each Experimental Event (3 Containers Pooled);

FIG. 7 depicts Diagram 3: Log 10 Head Capsusle Width Distribution for Each Event (3 Containers Pooled);

FIG. 8 depicts Diagram 4: Quantile-Quantile Plots Comparing the Distribution of Instars (Converted to Quantiles) Between the Reference (Control) and Experimental Events B and C;

FIG. 9 depicts Diagram 5: Separate Kaplan-Meier estimates of the complimentary (i.e., survival) cumulative distribution of head capsule widths by event; and FIG. 10 depicts Diagram 6: Average (±S.D.) number of western corn rootworm larvae recovered from the miniaturized version of the sublethal seedling assay.

DETAILED DESCRIPTION OF THE INVENTION

The present inventions now will be described more fully hereinafter with reference to the accompanying drawings, in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present invention provides methods and compositions for evaluating the efficacy of a plant protection mechanism against immature insects. One embodiment of the invention is schematically illustrated in FIG. 1. Such a method as shown in FIG. 1 provides an assay function for increasing the precision of, for instance, trait evaluation and resistance monitoring with respect to an insect such as, for example, the corn rootworm. In one embodiment, such a method involves evaluating a protected plant having a protection mechanism. A population of immature insects (i.e., nymphs or larvae) belonging to an insect species having a plurality of instars (i.e., more than one instar) is first exposed to the protected plant such that the protected plant is at least contacted thereby (i.e., contact with or ingestion of the protected plant by the insects). The exposure extends for a selected time period, corresponding to a sublethal exposure of the insect population to the protected plant. That is, for example, the exposure of the insect population may extend for sufficient time to allow some development of the insects (i.e., through the instars), but not into the pupal or adult stage of development. Thus, the term "immature insect" as used herein refers to insects that are in either the larval or nymphal stage of development. With respect to the "sublethal" aspect of the exposure, the time period for exposure, in one advantageous embodiment, is selected to maximize the duration of insect development such that differences in insect development within the population resulting from exposure to different protection mechanisms are statistically distinguishable. The term "sublethal exposure" as used herein indicates that the exposure time period is set so that most of the insects do not die during the exposure time period. Thus, in some embodiments, more than 50%, 60%, 70%, 80%, 90%, 95%, or 99% of the insects do not die during the exposure time period. The exposure time period is also selected to expire before substantially all of the insect population leaves the larval or nymphal development stage, after which measurements of physical characteristics are less meaningful to a sublethal assay. Thus, in some embodiments, the time period for exposure will expire before more than 90%, 95%, or 99% of the insect population leaves the larval or nymphal development stage. In some embodiments of the invention, different insect populations are exposed to the plant for different periods of time.

The exposure of the insect population to the protected plant is then halted following the selected time period. That is, while the insect population is still alive and being exposed to the protected plant, the exposure is halted for the entire population in a simultaneous or substantially simultaneous manner, for example, by simply removing the insects from the protected plant or by killing the population through immersion in ethyl alcohol, exposure to high concentrations of carbon dioxide, or some other suitable method. In some embodiments, insects are killed after removal from exposure to the protected plant. Once the exposure to the protected plant is terminated, the insects are collected and counted, a physical characteristic of at least some of the insect larvae or nymphs is measured, and the insect population is then sorted into the instars based on the measured physical characteristic.

One such physical characteristic may comprise, for example, a head capsule width, where the insect is a corn rootworm. Other suitable physical characteristics for use in the methods of the invention correlate with the stage of larval or nymphal development and/or with a particular instar. Such suitable physical characteristics include, for example, head capsule length, head capsule circumference, and head capsule volume as well as other measurable physical characteristics such as hormone or enzyme levels. Measurements may be made in any suitable manner. For example, it may be useful to use an optical grid or a micrometer for microscopic measurements. As described below, another measured physical characteristic may be larval body size.

The measured physical characteristics of the insect population may then be statistically analyzed, in some embodiments across the instars, so as to determine efficacy of the trait of the protected plant with respect to the insect population. For example, the statistical analysis may involve analyzing the number of insect larvae or nymphs recovered or collected upon terminating the exposure. In other instances, the statistical analysis may involve determining the distribution of the measured physical characteristics with respect to the instars. In some instances, such a statistical analysis may be performed in comparison to a selected control entity. See, for example, the comparison of the distribution of recovered insects from transgenic versus non-transgenic plants across instars (as determined, for example, by measuring the head capsule width) as shown generally in FIG. 3.

According to some method embodiments, wherein the statistical analyses are performed, for example, in comparison to a selected control entity, a distribution of collected insects (across instars, for example) for an experimental group and a corresponding distribution of collected insects (across instars, for example) for the control entity may be systematically compared using one or more statistical techniques that may be used to produce a quantitative result that summarizes, for example, the differences in insect number distribution (across instars, for example) of the experimental group and the control entity. For example, one skilled in the art will appreciate that a traditional method for comparing a set of frequency distributions is the chi-square test for association, also known as contingency table chi-square, which can be used to test whether any set of frequency distributions are the same regardless of the shape of the distribution. Another test that may be useful for comparing the head capsule distribution of a control population versus that of an experimental population is the non-parametric two-sample Kolmogorov-Smirnov (K-S) test. The K-S test may evaluate whether the two distributions are from the same distribution, and makes no assumptions about the shape of the distribution. In some other embodiments, the Quantile-Quantile plot technique (see Johnson, R. A. and D. W. Wichern, Applied Multivariate Statistical Analysis, $5^{th}$ Ed., (Prentice Hall, N.J. 767 pp. ISBN 0-130-92553-5. 2002)) may be used to compare the insect measurement distributions (across instars, for example) of a control group and an experimental group. An example of the results of such an analysis as applied to different insect populations collected according to various embodiments of the present invention is shown generally in Diagram 4 of the Example 1. In yet another embodiment, the various measurement (such as head capsule width, for example) distributions may be treated as survival distributions. One skilled in the art will appreciate that the nonparametric product limit or Kaplan-Meier test may then be used to compare the survival distributions.

Graphical analyses, including a frequency histogram of the measured physical characteristics (such as head capsule with plotted across instars, for example) for each treatment plotted on the same scale, may provide indicators of shifts, trends and differences among treatments, as well as evidence of the effects of random variation and sample size. For example, as shown in Example 1, Diagram 2, histograms of head capsule width for larvae exposed to each corn trait in the data set given in Table 1 for the western corn rootworm (WCRW) (*Diabrotica virgifera* LeConte [Coleoptera: Chrysomelidae]) may be plotted. In the particular experimental example shown, it should be noted that the method of the present invention yielded an indication that the distribution of head capsule widths for larvae exposed to plants containing each trait shifted to the smaller head capsule sizes and fewer individuals made it to the larger head capsule sizes (i.e. later instars) or presumably even survived compared to the CONTROL larvae exposed to plant material from a plant which did not contain any plant protection mechanism.

Other analysis types, such as parametric mean separation methods, may be used to test whether the means of two or more measurement distributions (across instars, for example) are the same. Furthermore, because of the multimodal distributional aspects of some data that may be collected as part of the measuring steps of the present invention, a nonparametric test (such as, for example, a Wilcoxon-based nonparametric method) may serve as an alternate approach to determine if two populations have the same central tendency.

Various analysis and/or graphical tools may be used to generate statistical analyses of the measured physical characteristics (across instars, for example) of at least some of the collected insects. For example in some method embodiments, the MINITAB statistics package (Minitab Inc., MINITAB Statistical Software, Release 13.32. Minitab Inc, State College, Pa. 16801. 2000.) may be useful performing many of the statistical analyses disclosed above and discussed in further detail in the Experimental Example 1. Other statistical analysis techniques, such as the Kologorov-Smirnov Test and the Quantile-Quantile plot technique, for example, may be implemented using other software packages including, but not limited to SAS 9.1 (SAS Institute Inc., SAS System for Windows, Release 9.1. SAS Institute Inc., Cary, N.C. 2002-2003.).

A "plant protection mechanism" (otherwise referred to herein as a "protection mechanism"), as used herein, may include any character, trait, or treatment that decreases or is intended to decrease insect damage to a plant. Thus, for example, a plant protection mechanism may be: a native plant gene that reduces insect-caused injury to plants; a transgenic trait; a specimen; an event resulting from an associated transformation process that reduces insect-caused injury to plants; or a chemical applied at any rate to the seed, soil or plant; or combinations thereof. The term "plant characteristic," as used herein, may include genetic variations of the same plant species (e.g., hybrids, varieties, or cultivars), native plant genes or transgenic traits (e.g., herbicide resistance genes, drought tolerance genes, nutritional quality genes) used for purposes other than protection of the plant from insects, chemicals applied to the seed, soil or plant (e.g., fungicide or herbicide) not intended to protect plants from insect-caused injury, or combinations thereof that may interact with a plant protection mechanism. The term "protected plant" as used herein refers to a plant being evaluated for the presence and/or efficacy of a trait or protection mechanism. In some embodiments, a protected plant has a trait which is an effective protection mechanism.

As used herein, the term "plant" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

Examples of methods according to the present invention, as further described herein, are generally presented in terms of a corn rootworm type of insect exposed to a transgenic corn plant including a trait for insect control (such as corn rootworm control). However, though presented solely for the sake of example, one skilled in the art will appreciate that such methods may be accomplished with many different types or species of insects and with many different plants and associated plant protection mechanisms. Accordingly, the corn rootworm type of insect and the transgenic corn plant discussed herein are not intended to be limiting in any respect in regard to the applicability of the methods disclosed and/or claimed in the present invention.

As such, exemplary studies used in the development of the present invention involve exposing a population of corn rootworm to protected corn plant seedlings having a trait of interest and another population to a non-protected control entity or other "control entity" or "control." Such a control entity may comprise, for example: insect nymphs or larvae of the insect species exposed to a different specimen of the protected plant having the protection mechanism; insect nymphs or larvae of the insect species exposed to a non-protected plant; insect nymphs or larvae of a different insect species exposed to the protected plant; insect nymphs or larvae of the insect species exposed to a selected specimen of the protected plant; insect nymphs or larvae of the insect species exposed to the protected plant having a selected protection mechanism; insect nymphs or larvae of the insect species exposed for a lesser duration to the protected plant having the protection mechanism; and/or insect nymphs or larvae of the insect species exposed to the protected plant having the protection mechanism and a selected plant characteristic.

The exposure extends for a prescribed or selected period of time sufficient to create a distribution of different nymphal or larval development stages as measured by the amount of recovered insect nymph or larvae and a physical characteristic of the insect, such as insect head capsule width. The frequency distribution of head capsule widths (across instars)

can then be compared to the frequency distribution in a control population exposed to plants that have no adverse impact on the insects and/or plants that have other traits of interest affecting the corn rootworm. In line with such a statistical analysis, embodiments of the present invention examine small shifts in nymphal or larval development as determined from the analysis of amount of recovered insects and the distribution of the measured physical characteristic(s) of the insect, such as head capsule width, to identify subtle differences in efficacy between, for example, traits of the transgenic plant, traits of transgenic plants that were obtained from different transformation events with the same or similar transformation construct, or stacked traits where the presence of more than one trait may have a significant effect on the combined efficacy of the traits. Such a method may also be useful, for instance, for contrasting efficacy of the same plant trait or transformation event against different insect species, such as between rootworm species, for estimating the efficacy of a plant trait against the target pest, and for identifying insect populations or species that have developed resistance to one or more particular traits in the protected plant.

As used herein, "efficacy" refers to the adverse impact of a plant characteristic, trait, and/or protection mechanism on the viability, health, and/or development of an insect exposed to it. For example, a plant protection mechanism has significant efficacy if it causes a significant distribution shift toward earlier instars in a population of nymphs or larvae exposed to a plant containing it in comparison to a population of nymphs or larvae exposed to an appropriate control plant. An adverse impact on insect viability, health, and/or development is present where there is any detectable negative impact on an insect, such as, for example, an increase in insect weight loss, a decrease in insect weight gain or feeding, an interference with the attraction of an insect to a plant, etc. Thus, a plant protection mechanism has efficacy if it has a detectable negative impact on an insect so that there is at least a 5%, 10%, 15%, 20%, 25%, 30%, 35%, 40%, 45%, 50%, 55%, 60%, 65%, 70%, 75%, 80%, 90%, 100%, 200%, 300%, 400%, or 500% or more difference between a population exposed to a plant containing the plant protection mechanism and a suitable control population (e.g., a population exposed to an appropriate control plant). A plant protection mechanism that has an efficacy is an effective plant protection mechanism. A plant protection mechanism that caused a significant distribution shift toward earlier instars in a population of immature insects exposed to it would be useful, for example, in delaying the maturity of the insect population so that damage from an adult population would be minimized and/or so that insecticides effective against the immature insects could be applied over a longer period of time.

As referred to herein, "dose" or "dosage" refers to the impact of a plant protection mechanism on the insect relative to survival of the insect on an unprotected plant. Dosage may be measured in some instances, for example, by measuring the level of expression of an insecticidal substance in the plant that is responsible for the protection mechanism; in other instances, dosage may be measured by the effect on the insect population or level of mortality that results from exposure to the protection mechanism.

Insect pests include any insect which has a larval or nymphal stage of development, including but not limited to insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; pest species in the family Elateridae, including species of the genera *Aeolus, Agriotes, Conoderus, Hemicrepidus,* and *Limonius; Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leu-*

*copterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

The terms "pesticidal activity" and "insecticidal activity" are used synonymously to refer to the activity of an organism or a substance (such as, for example, a protein) that has a detrimental effect on one or more particular pests and/or a particular insect. The detrimental effect of an organism or substance having pesticidal and/or insecticidal activity can be determined by any suitable measurement, including but not limited to: pest mortality; pest weight loss; pest attraction or repellency; and other behavioral and physical changes of a pest after feeding and exposure for an appropriate length of time such as, for example, a delay in pest development. For example, "pesticidal proteins" are proteins that display pesticidal activity by themselves or in combination with other proteins.

With respect to stacked traits, as referred to herein, one skilled in the art will appreciate that certain polynucleotides of a plant can be stacked with any combination of polynucleotide sequences of interest in order to create a transgenic plant with a desired trait. A trait, as used herein, refers to the phenotype conferred by a particular sequence or group of sequences. For example, some polynucleotides may be stacked with any other polynucleotides encoding polypeptides having pesticidal and/or insecticidal activity, such as other *Bacillus thuringiensis* toxic proteins (described, for example, in U.S. Pat. Nos. 5,366,892; 5,747,450; 5,737,514; 5,723,756; 5,593,881; and Geiser et al. (1986) *Gene* 48:109), lectins (described, for example, in Van Damme et al. (1994) *Plant Mol. Biol.* 24:825), pentin (described, for example, in U.S. Pat. No. 5,981,722), and the like. The combinations generated can also include multiple copies of any one of the polynucleotides of interest. Such polynucleotides can also be stacked with any other gene or combination of genes to produce a plant with a variety of desired trait combinations including, but not limited to, traits desirable for animal feed, such as high oil genes (e.g., U.S. Pat. No. 6,232,529); balanced amino acids (e.g., hordothionins as in, for instance, U.S. Pat. Nos. 5,990,389; 5,885,801; 5,885,802; and 5,703,409; barley high lysine (e.g., Williamson et al. (1987) *Eur. J. Biochem.* 165:99-106; and WO 98/20122); and high methionine proteins (e.g., Pedersen et al. (1986) *J. Biol. Chem.* 261: 6279; Kirihara et al. (1988) *Gene* 71:359; and Musumura et al. (1989) *Plant Mol. Biol.* 12:123)); and increased digestibility (e.g., modified storage proteins (e.g., U.S. application Ser. No. 10/053,410, filed Nov. 7, 2001); and thioredoxins (e.g., U.S. application Ser. No. 10/005,429, filed Dec. 3, 2001)). The disclosures of these exemplary references cited herein are incorporated herein by reference.

Certain polynucleotides can also be stacked with traits desirable for disease or herbicide resistance (e.g., fumonisin detoxification genes (e.g., U.S. Pat. No. 5,792,931); avirulence and disease resistance genes (e.g., Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance, such as the S4 and/or Hra mutations; inhibitors of glutamine synthase such as phosphinothricin or basta (e.g., bar gene); glyphosate resistance (EPSPS gene); and traits desirable for processing, or process products, such as high oil (e.g., U.S. Pat. No. 6,232,529); modified oils (e.g., fatty acid desaturase genes (e.g., U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (e.g., Schubert et al. (1988) *J. Bacteriol.* 170:5837-5847) facilitate expression of polyhydroxyalkanoates (PHAs)). In some instances, one could also combine certain polynucleotides with polynucleotides providing agronomic traits, such as male sterility (e.g., see U.S. Pat. No. 5,583,210), stalk strength, flowering time, or transformation technology traits, such as cell cycle regulation or gene targeting (e.g., WO 99/61619, WO 00/17364, and WO 99/25821). The disclosures of these exemplary references cited herein are also incorporated herein by reference.

Such stacked combinations can be created by any method including, but not limited to, cross-breeding plants by any conventional or TopCross methodology, or by genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

In one embodiment of the present invention, particularly in the step of exposing the population of insect nymphs or larvae to the protected plant, the insects are exposed to seedlings of the subject plant that are grown in a semi-natural environment favorable for both seedling and insect development. By implementing the semi-natural environment, limitations such as diet contamination for the insects that may occur in, for example, an artificial diet bioassay may be minimized or avoided. In the semi-natural environment, the insects are exposed to the protected plant such that exposure occurs at least through contact with (or through ingestion of) the protected plant by the insects. Such an exposure procedure allows for the efficient exposure of large numbers of insects to the protected plant over a relatively short duration. This provides an advantage in applications where sample size and method precision are critical, for example, in monitoring resistant insects.

The methods of the invention provide an enhanced ability to efficiently detect subtle differences in efficacy of a protection mechanism and/or pest susceptibility that may not be readily discernable using existing methods such as a root rating technique or an artificial diet bioassay. A suitable insect species for evaluation using the methods of the invention preferably exhibits a plurality of instars (i.e., larval or nymphal stages). With respect to corn plants, for example, various species of corn rootworm would be suitable, such as, for example, the northern and western corn rootworms as well as the southern corn rootworm (*Diabrotica undecimpuctata howardii*) and Mexican corn rootworm (*Diabrotica virgifera zea*), all of which have similar life cycles.

FIG. 2 illustrates an overview of the steps involved in executing an assay methodology as disclosed herein and according to one embodiment of the present invention. For all of the methods of the invention, it is understood that the particular steps may be performed in any order which accomplishes the objective of the method. Such a methodology as that illustrated in FIG. 2 may be adapted as necessary for specific insects, according to insect growth requirements known in the art; for example, a standard methodology for rearing western corn rootworm in the laboratory may be used (see, e.g., Branson et al. (1988) *J. Econ. Entomol.* 81: 410-414). In some instances, a 10¾×9¼×3½ inch clear plastic deli container with a hinged lid fit in a snap tight fit (e.g., Clear-View SmartLock Hinged Lock Containers, CI8-3035; PactIv Corp., Lake Forest, Ill.) may be used for the semi-natural environment for growing the subject plants. One assay methodology involves placing approximately 200 kernels of corn seed with a standard fungicidal seed treatment in the bottom of each container. Separate containers are established for the seed of the protected plant and for the control (e.g., a natural unaltered seed of the subject plant). Next, about 150 ml of a 1% fungicide solution (e.g., 3336F Turf and Ornamental Systemic Fungicide; Cleary Chemical, Dayton, N.J.) is added to each container.

Depending on the purpose of the assay, as described further below, the containers are filled with about 1,000 ml of either a plant growth media (e.g., Metro-Mix plant growth media) or loam-based potting soil. Immediately after adding the soil, pre-incubated corn rootworm eggs suspended in a 0.08% agar solution are dispensed onto the soil or plant growth media surface of each container. In order to obtain sufficient data, the egg-agar solution may be calibrated to deliver about 1,000 eggs per container. However, such a configuration may be appropriately scaled for larger or smaller quantities of seed and/or insect eggs as needed. Once prepared, the infested containers are closed and placed in an environmental chamber set at about 25° C., at about 65% RH (relative humidity), and with a photoperiod of about 14 hours light to 10 hours dark. In order to monitor egg hatch rate and viability within the infested containers, a subsample of eggs from the infestation process are reserved and plated onto moist filter paper in the bottom of agar-filled Petri dishes. The Petri dishes are then sealed with micro-pore tape, placed near the containers in the environmental chamber, and monitored for hatch. In some instances, the eggs are pre-incubated in such a way that first hatch typically begins within the containers at about 7 days after infestation. On the date of first hatch, the container lids are sealed shut to prevent insect escape, and a number of holes (e.g., about 12 holes of about 10 mm in diameter) are punched in the top of the lid for ventilation.

At this stage, the containers for an assay related to evaluating trait efficacy or resistance monitoring are handled in such a manner that insects are allowed to feed and develop in the containers for about 17 days after initial hatch. The plant growth media (e.g., Metro-Mix) is preferred in such instances. Following the development period (e.g., exposure of the larvae for a selected period so as to provide a sublethal exposure for the larvae), the "seedling mats" are then removed from the infested containers and each placed in a separate Berlese funnel to extract the insects. A Berlese funnel is an apparatus configured to extract and collect small insects from soil or decomposing litter. Above the funnel, a small lamp with a low-power incandescent light bulb, or other heat source, heats and dries the seedling mat, thereby forcing the insects downward into a collection container that contains a substance lethal to the insects such as, for example, ethyl alcohol. In this manner, the insect population is simultaneously or substantially simultaneously killed without physically destroying the insect specimens. In this manner, the exposure of the insects to the protected plant is halted while also halting the development of the insects.

However, there may also be instances where the exposure is halted, for example by removing the insects from the protected plant, and the necessary analysis of the insect population accomplished while the insects are still alive, but prior to further insect development. Once the exposure is halted, the insects are then counted and categorized into one of three immature stages of development (e.g., instars characteristic of corn rootworm) by measuring a physical characteristic such as, for example, the width of the head capsule of the insect as determined, for instance, under a dissecting microscope. Such a study may have data requirements for analysis including, for example, estimating the proportion of live nymphs or larvae per container and measuring head capsule widths on a minimum of 17 larvae per container and a minimum of 3 containers per treatment for both transgenic and nontransgenic (control) hybrids. Depending on the requirements of the study, the number of immature insects that are collected and the number of immature insects for which a physical characteristic is measured may vary accordingly. Thus, it may be necessary only to collect and/or measure at least some of the immature insects in order to evaluate a protected plant. One of skill will be able to select the appropriate number of insects to be collected and/or measured in accordance with the requirements of the study and the statistical analysis to be performed.

One skilled in the art will appreciate that although some embodiments described herein use a relatively large input of plants and insects, the invention is not restricted to applications where there is no limit to seed number and/or insect number. Various embodiments of the invention which use a miniaturized version of the test system (also referred to herein as the "mini-system") were developed to improve the methods for use in situations where either the quantity of corn seeds or corn rootworm eggs were limiting. In such embodiments, the insect population may be smaller, for example, the insect population may comprise fewer than 500, 400, 300, 250, 200, 150, 100, 50, or fewer insects. Similarly, in such embodiments, the step of exposing the insect population to the protected plant may comprise exposing the population to fewer than 1,000; 500; 400; 300; 250; 200; 150; 100; or 50 or fewer plants (e.g., seeds).

Another advantage of the present invention is that it can be used to evaluate the efficacy of a protection mechanism which is a transgene (e.g., a polynucleotide encoding an insecticidal protein). In one embodiment of the invention detailed herein, populations of neonate corn rootworm are exposed to corn seedlings expressing the transgene of interest and a control entity. An exposure period is selected to maximize the duration of exposure of the immature insect to the protected plant so as to maximize the differences in developmental rates of the insects between plant treatments; here, the exposure period is about 17 days. Following the exposure period, a count of the total amount of recovered larvae is made and the distribution of the exposed population among the three stages of rootworm larval development is determined by measuring at least one physical characteristic of the larvae. For example, the insect head capsule width may be the measured physical characteristic, though many other physical characteristics of the insect may be used instead of or in addition to head capsule width.

Rootworms are genetically programmed to complete 3 stages of larval development or instars. At a constant temperature of about 21° C., the $1^{st}$, $2^{nd}$, and $3^{rd}$ instars of the western corn rootworm generally complete development in 6, 5, and 12 days, respectively (see, e.g., Jackson and Elliott (1988) *Env. Entomol.* 17: 166-171). In comparison, northern corn rootworm development at about 21° C. is somewhat slower, with $1^{st}$, $2^{nd}$, and $3^{rd}$ instars generally completing development in 7, 7, and 19 days, respectively (see, e.g., Woodson and Jackson (1996) *Ann. Entomol. Soc. Am.* 80: 226-230). In general, the cooler the temperature, the longer it takes for the larvae to complete a development stage, and vice versa. In some instances, the developmental stage or instar of the insect can be determined using a measured physical characteristic of the insect (see, e.g., methods described by Hammack et al. (2003) *J. Econ. Entomol.* 96: 1153-1159.). For example, for the corn rootworm, larvae with a head capsule width of less than about 270 µm are classified as being in the $1^{st}$ instar. Larvae with a head capsule width of between about 270 µm and about 410 µm are designated as being in the $2^{nd}$ instar. Insects within the $3^{rd}$ instar have a head capsule width greater that about 410 µm. Both northern and western corn rootworms have been shown to have a similar head capsule width for each instar. Methods and criteria for identifying the various instars for a particular species are known in the art.

Once the frequency distribution of head capsule widths for the insect population exposed to plant material from plants containing a particular trait is determined, this frequency distribution is then compared with the frequency distribution of head capsule widths for insects exposed to appropriate control plant material ("control entity"). This comparison allows detection of small shifts in development in an insect population as indicated by a shift in the frequency distribution of head capsule width. In this manner, the methods of the invention are useful for identifying, for example, subtle differences in efficacy among or between plant protection mechanisms.

These small shifts in development of the immature insect population can also distinguish between, for example: the efficacy of different transformation events; the efficacy of a plant protection mechanism in different plants obtained using the same transformation construct; and the efficacy of stacked traits where expression of multiple traits may or may not have a synergistic effect. In addition, the methods of the invention may also be useful for: contrasting efficacy among or between rootworm species of a particular trait or transformation event; estimating the dosage of a trait; identifying synergistic or antagonistic interactions of plant protection mechanisms when such mechanism are used together; and identifying insects that have developed resistance to certain traits.

In one example, FIG. 3 illustrates a distribution of larval head capsule widths for corn rootworm after 17 days of exposure to protected transgenic corn plants and to control plants. The data shown in FIG. 3 illustrate a shift in development toward the $1^{st}$ and $2^{nd}$ instars of the insect population exposed to the transgenic plant. This shift in the frequency distribution of head capsule sizes in insects exposed to a protected plant in comparison to the distribution for larvae exposed to the control entity indicates that the plant protection mechanism of the protected plant was effective. Such a protection mechanism may retard the development of the exposed insect population to the extent that it provides a level of protection to the plant which is commercially useful.

In some instances, the methods of the invention may also be used to provide a comparison between the susceptibility of a laboratory-prepared (e.g., "semi-natural") insect population and a field-collected insect population, or between field-collected insect populations. In such evaluations, a protection mechanism with less efficacy would produce a frequency distribution in the insect population more similar to that of the insect population that was exposed to the unprotected control plant.

The development of insect resistance to a plant comprising a protection mechanism which is a transgene depends, for instance, on the genotype and phenotype of resistant insects, which is another factor that may be evaluated using methods of the present invention. In some embodiments, methods of the present invention allow a laboratory simulation of expected field results for the impact of a particular plant trait of interest on selected insect resistance alleles. Further, for example, subsequent generations of an insect of interest such as corn rootworm can all be exposed to seedlings having a particular protection mechanism using the methodology previously discussed. Individual insects that survive the exposure and develop to adulthood can be subsequently intermated and the progeny resulting from such inter-mating then used in a new test against plants containing the same protection mechanism. This exposure of successive generations of insects to the same protection mechanism can be used to evaluate the possibility of the development of resistance by the insects to the protection mechanism. In the same manner, embodiments of the present invention also allow selection and evaluation of resistant insects from the field. Accordingly, embodiments of the present invention described herein may facilitate a rapid description of the genetics or other mechanisms conferring resistance of insects to protected plants.

In some embodiments, the analysis of gathered instar data may also include determining an "odds ratio." An example of an equation for an odds ratio is shown below. In such embodiments, head capsule widths are measured under a microscope. In particular, head capsule widths are measured using an ocular grid placed in an eyepiece of the microscope. In some embodiments, for example, the ocular grid may be 10×10 mm with 0.5 mm divisions at a magnification of 64×. Each larva is placed flat on the microscope stage and the widest point of the head capsule is measured. Head capsule width measurements are then translated into instars (e.g., 1st, 2nd, and 3rd), and a statistical model is used to estimate the proportions of the instars for each treatment. In various embodiments, these may include estimating proportions of instars for insects subjected to a protected plant ("protected proportions" as referred to in the equation) and estimating proportions of instars for insects subjected to a control ("control proportions" as referred to in the equation). In some embodiments, the odds ratio may be estimated using the statistical model. In other embodiments, the odds ratio may be calculated manually, or in some other manner. It should be noted that in the depicted embodiment, the proportions are calculated for the 3rd instar, however in other embodiments, in addition to (or in place of) this calculation, other instar proportions may be calculated (e.g., for the 1st and/or 2nd instars).

$$\left. \begin{array}{l} \dfrac{\text{control proportion}^* \text{ of } 3^{rd} \text{ instar}}{1 - (\text{control proportion}^* \text{ of } 3^{rd} \text{ instar})} = \text{odds for control} \\ \dfrac{\text{protected proportion}^* \text{ of } 3^{rd} \text{ instar}}{1 - \text{protected proportion}^* \text{ of } 3^{rd} \text{ instar}} = \text{odds for protection} \end{array} \right\}$$

$$\dfrac{\text{odds for protection}}{\text{odds for control}} = \text{odds ratio}$$

*In the depicted embodiment, proportions and odds ratio estimated by statistical model (SAS PROC GLIMMIX)

In various embodiments, Applicants have found that an odds ratio of less than 1.0, indicates that insects exposed to the protection mechanism developed slower than the control insects. Applicants have also found that the smaller the odds ratio, the greater the effect of the protection mechanism and thus the greater the efficacy of the protection mechanism of the protected plant.

Another measured physical characteristic may be larval body size. In such embodiments, larval body size may be determined in some manner. For example, in some embodiments one or more images containing larval samples may be captured (such as, for example, by scanning the image using a flatbed scanner). FIG. 4A depicts an example of a scanned image of the collected larvae. After the image has been captured, the captured image is imported into an image analysis software program configured to separate the larvae from the background image and measure the larval body size. The image analysis software program may measure the larval body size in a variety of ways, however in the depicted embodiment the larval body size is measured in pixels. The pixel measurements may then calibrated for a length measurement (such as, for example, millimeters). The larval body size may be converted into a variety of measurements for analysis, however in the depicted embodiment a mean area of larvae is then calculated based on the measured larval body size.

FIG. 4B depicts an example of isolation of the larvae from a background image as performed by the image analysis software. As shown in the drawing, in various embodiments the image analysis software may establish a border around each larva in the captured image in order to separate the larvae from the background image (background image shown in black in the figure) and to calculate the mean area of larvae (or other measurement based on larval body size). As such, a difference may be established between insects subjected to a protected plant and insects subjected to a control (mean area of larvae subjected to control−mean area of larvae subjected to the protected plant). In such a manner, the greater the difference between the mean area of the larvae subjected to the control and the mean area of the larvae subjected to the protected plant, the greater the effect of the protection mechanism.

In consideration of the methodology previously described, representing various embodiments of the present invention, the example presented below illustrates one application of the methodology. One skilled in the art will appreciate, however, that this example, as well as other examples presented herein, are not intended to be limiting in any manner with respect to the applicability of the principles addressed herein.

EXAMPLE

The following demonstrates methodology for one application of the present invention. Treatments included seeds from control or reference corn (CONTROL) and three protected plants which comprised experimental transgenic corn events (i.e., EXPERIMENTAL EVENT B, EXPERIMENTAL EVENT C and EXPERIMENTAL EVENT D). The protection mechanisms were tested for efficacy against corn rootworm larvae. The test system utilized 10¾×9¼×3½ inch clear plastic deli containers with hinged lids that snapped closed. Setup involved adding 150 ml of pre-germinated corn seeds to the bottom of each plastic deli container. A total of 3 containers were set up for each treatment. Next, 150 ml of a 1% systemic fungicide solution was added to each container. Each container was then filled with 1,000 ml of dry Metro-Mix 200 plant growth media. Immediately after adding the growth media, western corn rootworm eggs suspended in a 0.08% agar solution were dispensed onto the soil surface of each container. A total of 2,000 eggs were exposed to each CONTROL container and 10,000 eggs to each container with EXPERIMENTAL EVENTS B, C, and D. The infested containers were placed in an environmental chamber at a temperature of 25° C., relative humidity of 65%, and a photoperiod of 14 hours light:10 hours dark. The exposure period was halted on day 28 (i.e., when the insects had spent 11 days as eggs and 17 days as larvae) by removing the contents of each container and placing it in a separate Berlese funnel to extract the corn rootworm larvae.

All larvae collected from each container were counted. A random sub-sample of 25 larvae per container was selected and the physical characteristic of head capsule width was measured using a dissecting microscope. Head capsule widths were measured to the nearest 0.001 inch. These sub-sampled larvae were then assigned to 1 of 3 instars based on the width of their head capsule. First instar larvae had head capsule widths less than 0.011 inches, second instar larvae had head widths between 0.011 and 0.016 inches, and third instar larvae had head widths greater than 0.016 inches. A detailed summary of the data, the statistical analysis, and interpretation of results are discussed later in this example.

One skilled in the art to which this invention pertains would appreciate that the methodology described above used a relatively large input of corn seed and corn rootworm eggs. Accordingly, a "mini-system" embodiment of the invention was also tested. In this example, treatments included either 15, 18, 25, or 35 seeds from control or reference corn (CONTROL). The test system consisted of a 2-piece clear plastic container. The bottom piece was 3¼ inches tall and 4 inches in diameter at the top, holding a volume of approximately 100 ml. The top piece of the container snapped onto the base and was 8 inches tall. A total of 3 containers were set up for each treatment.

Setup involved adding 10 ml of a 1% systemic fungicide solution to the base of each container. Next, CONTROL seeds were added to the containers depending on the treatment (here, 15, 18, 25, or 35 seeds). Each container was then filled with 100 ml of dry Metro-Mix 200 plant growth media. Immediately after adding the growth media, western corn rootworm eggs suspended in a 0.08% agar solution were dispensed onto the soil surface of each container. A total of 200 eggs were added to each container with 15, 25, and 35 corn seeds. Only 150 eggs were added to the containers with 18 corn seeds. The infested containers were placed in a walkin environmental chamber at a temperature of 25° C., 65% relative humidity, and a photoperiod of 14 hours light:10 hours dark. The exposure period was halted on day 19 (here, after the insects had spent 2 days as eggs and 17 days as larvae) by removing the contents of each container and placing it in a separate Berlese funnel to extract the corn rootworm larvae. All larvae collected from each container were counted. A random sub-sample of 25 larvae from the containers with 18 kernels was selected and the physical characteristic of head capsule width was measured using a dissecting microscope. Head capsule widths were measured to the nearest 0.001-inch and assigned to 1 of 3 instars using the procedure described above.

The average number of larvae recovered from each mini-container with 15, 18, 25, and 35 corn seeds are depicted in Diagram 6. Even when only 15 corn seeds were used, an average of 60 larvae per container were recovered. This was more than double the number of larvae necessary to conduct a valid statistical analysis of head capsule distributions. Table 9 provides the descriptive statistics for larval head capsule widths obtained from the treatment containing 18 CONTROL corn seeds and 150 rootworm eggs. These data showed that head capsule widths averaged 0.019 inches, which was equivalent to the width of a $3^{rd}$ instar larva. This result indicated that the mini-version of the test system was capable of producing larvae that were equivalent in development for the exposure period tested compared to larvae produced on CONTROL corn seed in the full-size version of the test system (See Table 1 for descriptive statistics of CONTROL larvae in full-size system). Additionally, the variation (i.e., standard deviation, standard error, minimum and maximum estimates of head width) in head capsule widths obtained from the mini-system were less than that obtained in the full-size system (see Table 1 for descriptive statistics for the full-size system). The increased level of precision demonstrated with the miniaturized version of the present invention adds value to those applications where sample size may be limited due to having only small quantities of corn seed or corn rootworm eggs available.

The distribution of Western Corn Rootworm (*Diabrotica virgifera* LeConte [Coleoptera: Chrysomelidae]) head capsule widths resulting from the rootworm being reared on a control or reference corn (CONTROL) and 3 experimental events (i.e., EXPERIMENTAL EVENT B, EXPERIMENTAL EVENT C and EXPERIMENTAL EVENT D) was analyzed using a number of statistical methods. The analyses of the insects, as described herein, demonstrated that EXPERIMENTAL EVENT B and EXPERIMENTAL EVENT C differed from the control at the 95% confidence level. The EXPERIMENTAL EVENT D strain differed at the 90% confidence level, and in some instances, at the 95% confidence level. The variation for the EXPERIMENTAL EVENT D strain was attributable to, for example, low survival resulting from the high efficacy on the EXPERIMENTAL EVENT D strain. Two methods used for analyzing the collected data and comparing the distributions were the two-sample Kolmogorov-Smirnov test and the Quantile-Quantile plot technique. The Maim-Whitney U test and the analogous Kruskal-Wallis tests for multiple samples, which test for equal medians, were also investigated and may be useful for screening plant protection mechanisms. These statistical methods are appropriate for analysis of insect head capsule width measurements for populations exposed to different treatments. They were applied here to compare the effects on head capsule size of different corn transgenic events that provide protection from corn rootworm (*Diabrotica* spp.) larval feeding in a laboratory environment.

After hatching from the egg, insects go through a series of immature stages before pupating and developing to the adult stage. Because insects possess exoskeletons, a new head capsule is formed with each molt to a new stage (instar), and the head capsule does not change in size until another molt or progression to a further instar. The body of an insect larva expands as the larva increases in size between molts. The width of a head capsule typically increases 1.2-1.4 fold in a geometric fashion with each increasing instar. This geometric progression of head capsule widths is referred to as Dyar's rule (see, e.g., Borror, D. J., D. M. DeLong and C. A. Triplehorn, Introduction to the Study of Insects, 5th Edition. Holt, Rinehart and Winston, N.Y. ISBN 0-03-043531-5. 1998). There is normal variability in head capsule width among individuals within a population within a specific instar. Accordingly, the distribution of head capsule widths is set of multimodal peaks, each peak with a normal distribution around a distinct width (Hammack et al. (2003) *J. Econ. Entomol.* 96: 1153-1159). The relative size of the instar frequency distributions continually changes as the age structure of the population changes. Both direct (e.g., toxicity or growth enhancement) and indirect (e.g., antifeedant) effects of a plant protection mechanism may change the rate of development, and thus head capsule width, within a population. Accordingly, when immature insects are exposed to and/or consume an insect-protected plant, the distribution of head capsule widths in that population is shifted toward earlier instars relative to the distribution of head capsule widths in a population exposed to a non-protected plant or other control (control). Under such a premise, a greater difference in head capsule widths between protected and unprotected plants is indicative of a greater level of efficacy in the protected plant.

Analysis Methods

As follows, all analysis and graphics were generated using the MINITAB statistics package (Minitab Inc., MINITAB Statistical Software, Release 13.32. Minitab Inc, State College, Pa. 16801. 2000.), except for the Kologorov-Smirnov Test and the Quantile-Quantile plot technique which were implemented using SAS 9.1 (SAS Institute Inc., SAS System for Windows, Release 9.1. SAS Institute Inc., Cary, N.C. 2002-2003.). Unless specifically referenced otherwise, detailed descriptions of the techniques used can be found in Miller, R. G., Jr., Beyond ANOVA, Basics of Applied Statistics (John Wiley & Sons, N.Y. 317 pp. ISBN 0-417-81922-0.1986.), Sokal, R. R. and F. J. Rohlf, Biometry, $2^{nd}$ Edition (W. H. Freeman and Co., N.Y. 859 pp. ISBN 0-7167-1254-7. 1981) or Johnson, R. A. and D. W. Wichern, Applied Multivariate Statistical Analysis, $5^{th}$ Ed., (Prentice Hall, N.J. 767 pp. ISBN 0-130-92553-5. 2002).

This analysis assumes no significant effect of the container on head capsule distribution, and is demonstrated graphically in Diagram 1.

Graphical analyses, including a frequency histogram of the head widths plotted for each treatment on the same scale, may provide indicators of shifts, trends and differences among treatments, as well as evidence of the effects of random variation and sample size. Diagram 2 presents histograms of head capsule width for larvae exposed to each corn trait in the data set given in Table 1 for the western corn rootworm (WCRW) (*Diabrotica virgifera* LeConte [Coleoptera: Chrysomelidae]) head capsule widths. Of note is that the distribution of head capsule widths for larvae exposed to plants containing each trait shifted to the smaller head capsule sizes and fewer individuals had larger head capsule sizes (i.e., were from later instars) compared to the CONTROL larvae exposed to plant material from a plant which did not contain any plant protection mechanism.

Parametric Mean Separation

One method of comparing distributions is to test whether the means of the distributions are the same. If the treatment reduces head capsule width, then the mean of the distribution for a treatment where the subjects are exposed to a trait conferring crop protection should be smaller than the mean for the CONTROL. Because the variance may be expected to be proportional to the mean, a logarithmic transformation before analysis with the standard t-test or ANOVA, or a Welch's t' test (see Miller 1986) for samples with unequal variance, may be applied. See Diagram 3, for example. The t and t' tests are relatively robust, so departure from the assumption of normality should only have modest effects. (This is because the asymptotic means will be approximately normal even if the parent distributions are not.) The variances can be expected to be similar on the logarithmic scale if the Coefficients of Variation (CV) are approximately the same for each trait.

The results of the t-test on the Log 10 transformed head capsule widths are shown in Table 2. In all cases, the null hypothesis was that the reference (i.e., CONTROL) had mean head capsule widths less than or equal to the treatment mean. The alternative hypothesis was that the reference mean was greater than the treatment mean. The mean head capsule widths for the EXPERIMENTAL EVENT B and EXPERIMENTAL EVENT C were significantly greater than the reference mean at the 95% confidence level. The mean for the EXPERIMENTAL EVENT D line was not significant at the 95% confidence level, but was significant at the 90% confidence level. The results of Welch's t'-test on the untransformed data are shown in Table 3, wherein the means of all three events were significantly smaller than the corresponding reference CONTROL strain means at the 95% confidence level. The results of both tests suggests that the mean head capsule widths of immature insects reared on each of the traits were significantly less than those feeding on the control (CONTROL).

Wilcoxon-Based Nonparametric Methods

Because of the multimodal distributional aspects of the data, a nonparametric test may a better approach to determine if two populations have the same central tendency. Here inference is made regarding the median, rather than the mean. The traditional test is the Mann-Whitney form of the Wilcoxon rank test, which evaluates whether the medians of two populations are equal. As with the parametric case, the determination is whether the median of the reference line is greater than that of the experimental results. This test, however, assumes that both populations have the same shaped distribution which, in the head capsule case, should be true if the experimental trait has no impact on growth of immature insects exposed to it, but may have an impact in other instances. The analog for simultaneously testing several experimental strains at once is the Kruskal-Wallis test (see Miller 1986). This test has many advantages for sorting traits, and there are several methods for simultaneous multiple comparisons (again see Miller 1986). In any instance, the results of the comparisons of head capsule widths for each experimental event to the control using the Mann-Whitney test is shown in Table 4. Median head capsule width for immature insects (here, larvae) exposed to plant material from each experimental event was significantly different than the median width of immature insects exposed to the reference plant (control) at the 95% confidence level.

Comparing Distributions

One traditional method for comparing a set of frequency distributions is the chi-square test for association, also known as contingency table chi-square, which can be used to test whether any set of frequency distributions are the same regardless of the shape of the distribution. The test tends to be most robust when there are at least 5 counts in each cell of the contingency table. If the distributions being compared are not the same, then the squared difference between the observed frequency and the predicted frequency based upon the marginal probabilities becomes large. The sum of these squared deviations follows a chi-squared distribution, and allows the statistical significance of the difference between the two distributions to be tested. Table 5 includes the chi-square test for the head capsule width frequency for each experimental event compared to the control. The head capsule widths were grouped into three size categories, i.e., 0.005-0.010, 0.011-0.015 and 0.016-0.020, to increase the frequencies to more closely meet the assumptions of the analysis. This type of adjustment of categories to provide a better fit of data to an analysis method is generally known to those of skill in the art. Both the EXPERIMENTAL EVENT B and EXPERIMENTAL EVENT C had significantly different distributions than the CONTROL at the 95% confidence level. Although the comparison for the EXPERIMENTAL EVENT D did not meet the minimum frequency criteria for a reliable chi-square test it did have a relatively large chi-square suggesting that there likely was some difference.

Another test that may be useful to compare the head capsule distribution of the control versus that of an experimental event would be the non-parametric two-sample Kolmogorov-Smirnov (K-S) test. This test evaluates whether the two distributions are from the same distribution, and makes no assumptions about the shape of the distribution. Application of the K-S test using SAS Proc NPAR1WAY (SAS Institute 2002-2003) is shown in Table 6, wherein distribution of head capsule sizes from larvae exposed to all of the experimental trait lines were significantly different at the 95% confidence level. Accordingly, it can be assumed that none of the head capsule widths associated with the experimental lines had the same distribution as the control.

A third method to determine if two data sets come from the same distribution would be the Quantile-Quantile plot technique (see Johnson and Wichern, 2002). A quantile-quantile test is a method to compare the quantiles of the first data set against the quantiles of the second data set. If these two data sets come from the same distribution, the quantiles of the first data set should be similar to the quantiles of the second data set. In other words, if we plot the quantiles of the first data set against the quantiles of the second data set, the points should fall approximately on a 45-degree line and the correlation coefficient of these two data sets should be close to 1. The greater the departure from a 45-degree line, the greater the evidence for the conclusion that the two data sets are from two different distributions. Therefore, one may test the correlation coefficient between these two sets of quantiles. For example, one may conduct the test such that the null hypothesis states the correlation coefficient between these two quantiles are greater than or equal to 0.99. Note this null hypothesis is equivalent to saying the two data sets come from the same distribution.

Results from the application of the Quantile-Quantile test to the data set provided in Table 1 for western corn rootworm head capsule widths are shown in Table 7 and are plotted in Diagram 4. First, the head capsule widths were converted to ocular grid squares by multiplying head capsule width in inches by 322.67 (width of 1 ocular grid=0.078 mm). In all cases, the null hypothesis was the correlation between the quantiles of the first data set (i.e., REFERENCE POPULATION) and the quantiles of the second data set (i.e., EXPERIMENTAL EVENT) was greater than or equal to 0.99 (i.e., the two data sets come from the same distribution). The alternative hypothesis was the correlation between the quantiles of the first data set and the quantiles of the second data set was less than 0.99 (i.e., the two data sets come from two different distributions). When comparing EXPERIMENTAL EVENT B to the reference (i.e., CONTROL), the correlation coefficient between quantiles of EXPERIMENTAL EVENT B and quantiles of the REFERENCE is significantly less than 0.99 at 99% confidence level (P<0.0001), indicating these two head capsule width distributions are significantly different (i.e., have different levels of efficacy). Again, when comparing EXPERIMENTAL EVENT C to the REFERENCE (i.e., CONTROL), the correlation coefficient between quantiles of EXPERIMENTAL EVENT C and quantiles of the REFERENCE is significantly less than 0.99 at 99% confidence level (P<0.0001). When comparing EXPERIMENTAL EVENT B to EXPERIMENTAL EVENT C, the correlation coefficient between quantiles of EXPERIMENTAL EVENT B and quantiles of EXPERIMENTAL EVENT C is significantly less than 0.99 at 99% confidence level (P<0.0001). Note the median head width of EXPERIMENTAL EVENT B and the median head width of EXPERIMENTAL EVENT C are exactly the same (2.90). However, the mean head width of EXPERIMENTAL EVENT B is 3.64 and the mean head width of EXPERIMENTAL EVENT C is 3.49. A standard test of these means would indicate the events were not significantly different (t-test; t=0.868; df=2, 148; P=0.39). Therefore, the significant difference detected by the Quantile-Quantile plot technique resulted from a subtle shift toward larvae with smaller head capsule widths in EXPERIMENTAL EVENT C, and indicates a subtle increase in efficacy compared to EXPERIMENTAL EVENT B. Additionally, this example demonstrates the increased power associated with the sublethal seedling assay when the Quantile-Quantile test of distributions is used to detect subtle shifts in efficacy.

A final, less traditional method would be to treat the head capsule width distributions as survival distributions. Then the nonparametric product limit or Kaplan-Meier test can be used to compare the distributions. An example using MINITAB is shown in Table 8 and Diagram 5. As evident in Table 8, the EXPERIMENTAL EVENT B and EXPERIMENTAL EVENT C differed from the CONTROL at the 95% confidence interval with both the Wilcoxon and Log-Rank tests. The EXPERIMENTAL EVENT D differed based upon the Log-Rank test and was almost significant at the 95% confidence level using the Wilcoxon test.

Mixed Distribution Models

Another method that could be applied would be to fit mixed lognormal distributions directly using maximum likelihood estimation with a program such as SAS (SAS Institute, 2002-2003) or JMP (SAS Institute Inc., JMP User's Guide, Version 5. SAS Institute Inc., Cary, N.C. ISBN 1-59047-070-2. 2002.). The hypothesis that the distributions are the same could be tested using a likelihood ratio test for the reduced model (i.e., same mixed distribution for both head capsule data sets) versus the full model (i.e., completely separate distributions for the head capsules resulting from each event or the control). Such an approach would allow the distributions to be modeled completely so that relatively accurate predictions could be made if desired.

Conclusion

As shown, several statistical methods could be implemented to analyze whether the head capsule distributions of rootworms reared upon two or more insect-protected corn plants are statistically different. Selection of a method will depend upon the specific needs of the researcher conducting the study and the objects of such a study. As demonstrated with the EXPERIMENTAL EVENT B, EXPERIMENTAL EVENT C and EXPERIMENTAL EVENT D compared to the CONTROL, larvae exposed to plant material from each experimental event differed significantly from the CONTROL with every test method. The rootworms reared upon EXPERIMENTAL EVENT B and EXPERIMENTAL EVENT C were significantly different with every test. Those associated with EXPERIMENTAL EVENT D were occasionally only significant at the 90% confidence level, due mainly to the small sample size resulting from the greater efficacy and lack of survival of those rootworms reared on the EXPERIMENTAL EVENT D strain.

TABLE 1

Western Corn Rootworm (*Diabrotica virgifera* LeConte) head capsule widths (inches) by Experimental Event (Event B, Event C, Event D) and replicate (i.e., rearing container 1-3) with summary statistics.

Table 1. WCRW Larval Head Capsule Widths (inches)

| | Control-1 | Control-2 | Control-3 | B-1 | B-2 | B-3 | C-1 | C-2 | C-3 | D-1 | D-2 | D-3 |
|---|---|---|---|---|---|---|---|---|---|---|---|---|
| 1 | 0.02 | 0.007 | 0.009 | 0.009 | 0.009 | 0.009 | 0.009 | 0.009 | 0.009 | 0.012 | 0.013 | 0.013 |
| 2 | 0.009 | 0.009 | 0.009 | 0.009 | 0.014 | 0.009 | 0.009 | 0.009 | 0.011 | 0.013 | 0.012 | |
| 3 | 0.011 | 0.013 | 0.011 | 0.009 | 0.008 | 0.009 | 0.009 | 0.009 | 0.013 | | | |
| 4 | 0.008 | 0.014 | 0.011 | 0.009 | 0.009 | 0.009 | 0.009 | 0.009 | 0.012 | | | |
| 5 | 0.013 | 0.014 | 0.014 | 0.009 | 0.009 | 0.008 | 0.012 | 0.009 | 0.012 | | | |
| 6 | 0.013 | 0.012 | 0.014 | 0.009 | 0.009 | 0.009 | 0.009 | 0.012 | 0.009 | | | |
| 7 | 0.013 | 0.014 | 0.012 | 0.009 | 0.009 | 0.008 | 0.011 | 0.013 | 0.011 | | | |
| 8 | 0.012 | 0.012 | 0.018 | 0.009 | 0.014 | 0.009 | 0.012 | 0.009 | 0.008 | | | |
| 9 | 0.012 | 0.01 | 0.019 | 0.008 | 0.012 | 0.008 | 0.009 | 0.009 | 0.009 | | | |
| 10 | 0.02 | 0.01 | 0.018 | 0.014 | 0.012 | 0.009 | 0.009 | 0.012 | 0.009 | | | |
| 11 | 0.019 | 0.018 | 0.018 | 0.014 | 0.009 | 0.013 | 0.009 | 0.016 | 0.013 | | | |
| 12 | 0.019 | 0.018 | 0.02 | 0.009 | 0.012 | 0.008 | 0.012 | 0.012 | 0.014 | | | |
| 13 | 0.02 | 0.019 | 0.019 | 0.008 | 0.012 | 0.013 | 0.009 | 0.016 | 0.009 | | | |
| 14 | 0.019 | 0.018 | 0.018 | 0.013 | 0.009 | 0.014 | 0.014 | 0.016 | 0.011 | | | |
| 15 | 0.019 | 0.019 | 0.017 | 0.008 | 0.012 | 0.009 | 0.008 | 0.02 | 0.008 | | | |
| 16 | 0.02 | 0.018 | 0.018 | 0.008 | 0.012 | 0.012 | 0.009 | 0.016 | 0.014 | | | |
| 17 | 0.02 | 0.018 | 0.02 | 0.009 | 0.012 | 0.012 | 0.009 | 0.013 | 0.014 | | | |
| 18 | 0.019 | 0.019 | 0.018 | 0.009 | 0.013 | 0.009 | 0.013 | 0.005 | 0.014 | | | |
| 19 | 0.012 | 0.019 | 0.019 | 0.009 | 0.02 | 0.018 | 0.014 | 0.005 | 0.009 | | | |

TABLE 1-continued

Western Corn Rootworm (*Diabrotica virgifera* LeConte) head capsule widths (inches) by Experimental Event (Event B, Event C, Event D) and replicate (i.e., rearing container 1-3) with summary statistics.

| 20 | 0.02 |  | 0.019 | 0.019 | 0.019 | 0.018 | 0.011 | 0.009 | 0.011 |  |  |  |
|---|---|---|---|---|---|---|---|---|---|---|---|---|
| 21 | 0.019 |  | 0.018 | 0.014 | 0.012 | 0.012 | 0.01 | 0.009 | 0.009 |  |  |  |
| 22 | 0.019 |  | 0.012 | 0.009 | 0.018 | 0.009 | 0.02 | 0.009 | 0.008 |  |  |  |
| 23 | 0.019 |  | 0.007 | 0.008 | 0.019 | 0.009 | 0.012 | 0.008 | 0.013 |  |  |  |
| 24 | 0.018 |  | 0.017 | 0.014 | 0.019 | 0.018 | 0.009 | 0.008 | 0.013 |  |  |  |
| 25 | 0.018 |  | 0.019 | 0.019 | 0.009 | 0.009 | 0.009 | 0.008 | 0.013 |  |  |  |
| Avg. | 0.016 | 0.015 | 0.016 | 0.011 | 0.012 | 0.011 | 0.011 | 0.011 | 0.011 | 0.013 | 0.013 | 0.013 |

Descriptive Statistics: HW(Inches) by Event

| Variable | Event | N | Mean | Median | TrMean | StDev |
|---|---|---|---|---|---|---|
| HW(Inches) | Event B | 75 | 0.01128 | 0.00900 | 0.01100 | 0.00349 |
|  | Event C | 75 | 0.01083 | 0.00900 | 0.01066 | 0.00287 |
|  | Event D | 5 | 0.01260 | 0.01300 | 0.01260 | 0.00055 |
|  | Control | 70 | 0.01579 | 0.01800 | 0.01603 | 0.00396 |

| Variable | Event | SE Mean | Minimum | Maximum | Q1 | Q3 |
|---|---|---|---|---|---|---|
| HW(Inches) | Event B | 0.00040 | 0.00800 | 0.02000 | 0.00900 | 0.01300 |
|  | Event C | 0.00033 | 0.00500 | 0.02000 | 0.00900 | 0.01300 |
|  | Event D | 0.00024 | 0.01200 | 0.01300 | 0.01200 | 0.01300 |
|  | Control | 0.00047 | 0.00700 | 0.02000 | 0.01200 | 0.01900 |

TABLE 2 t-test on log 10 transformed head widths for the directional alternative $H_A: \mu_{CONTROL} > \mu_{E\#\#}$ vs $H_0: \mu_{CONTROL} \leq \mu_{E\#\#}$ Two-sample T for Log10 Control-width vs Log10 EXPERIMENTAL EVENT B-Width

|  | N | Mean | StDev | SE Mean |
|---|---|---|---|---|
| Log10 IS | 69 | −1.819 | 0.127 | 0.015 |
| Log10 E1 | 75 | −1.966 | 0.121 | 0.014 |

Difference = mu Log10 CONTROL-width − mu Log10 Event B-Width
Estimate for difference: 0.1460
95% lower bound for difference: 0.1119
T-Test of difference = 0 (vs >): T-Value = 7.08 P-Value = 0.000 DF = 142
Both use Pooled StDev = 0.124

Two-sample T for Log10 Control-width vs Log10 EXPERIMENTAL EVENT C-Width

|  | N | Mean | StDev | SE Mean |
|---|---|---|---|---|
| Log10 IS | 69 | −1.819 | 0.127 | 0.015 |
| Log10 E2 | 75 | −1.980 | 0.112 | 0.013 |

Difference = mu Log10 CONTROL-width − mu Log10 Event C-Width
Estimate for difference: 0.1603
95% lower bound for difference: 0.1274
T-Test of difference = 0 (vs >): T-Value = 8.07 P-Value = 0.000 DF = 142
Both use Pooled StDev = 0.119

Two-sample T for Log10 CONTROL-width vs Log10 EXPERIMENTAL EVENT D-Width

|  | N | Mean | StDev | SE Mean |
|---|---|---|---|---|
| Log10 IS | 69 | −1.819 | 0.127 | 0.015 |
| Log10 E3 | 5 | −1.9000 | 0.0190 | 0.0085 |

Difference = mu Log10 CONTROL-width − mu Log10 Event D-Width
Estimate for difference: 0.0805
95% lower bound for difference: −0.0145
T-Test of difference = 0 (vs >): T-Value = 1.41 P-Value = 0.081 DF = 72
Both use Pooled StDev = 0.123

TABLE 3

Welch's t′ test for the directional alternative $H_A: \mu_{CONTROL} > \mu_{E\#\#}$ vs $H_0: \mu_{CONTROL} \leq \mu_{E\#\#}$ Two-sample T for CONTROL-Width vs EXPERIMENTAL EVENT B-Width

|  | N | Mean | StDev | SE Mean |
|---|---|---|---|---|
| CONTROL-Widt | 69 | 0.01574 | 0.00397 | 0.00048 |
| EVENT B-Widt | 75 | 0.01128 | 0.00349 | 0.00040 |

Difference = mu CONTROL-Width − mu EVENT B-Width
Estimate for difference: 0.004459
95% lower bound for difference: 0.003423
T-Test of difference = 0 (vs >): T-Value = 7.13 P-Value = 0.000 DF = 135

Two-sample T for CONTROL-Width vs EXPERIMENTAL EVENT C-Width

|  | N | Mean | StDev | SE Mean |
|---|---|---|---|---|
| CONTROL-Widt | 69 | 0.01574 | 0.00397 | 0.00048 |
| Event C-Widt | 75 | 0.01083 | 0.00287 | 0.00033 |

Difference = mu CONTROL-Width − mu Event C-Width
Estimate for difference: 0.004912
95% lower bound for difference: 0.003948
T-Test of difference = 0 (vs >): T-Value = 8.45 P-Value = 0.000 DF = 123

Two-sample T for CONTROL-Width vs EXPERIMENTAL CONTROL D-Width

|  | N | Mean | StDev | SE Mean |
|---|---|---|---|---|
| CONTROL-Widt | 69 | 0.01574 | 0.00397 | 0.00048 |
| Event D-Widt | 5 | 0.012600 | 0.000548 | 0.00024 |

Difference = mu CONTROL-Width − mu Event D-Width
Estimate for difference: 0.003139
95% lower bound for difference: 0.002239
T-Test of difference = 0 (vs >): T-Value = 5.85 P-Value = 0.000 DF = 49

TABLE 4

Mann-Whitney U test for the directional alternative
$H_A: \epsilon_{CONTROL} > \epsilon_{E\#\#}$ vs $H_0: \epsilon_{CONTROL} \leq \epsilon_{E\#\#}$ Mann-Whitney Test and CI: CONTROL-Width, EXPERIMENTAL EVENT B-Width

| | | |
|---|---|---|
| CONTROL-Widt | N = 69 | Median = 0.01800 |
| Event B-Widt | N = 75 | Median = 0.00900 |

Point estimate for ETA1 - ETA2 is 0.00500
95.0 Percent CI for ETA1 - ETA2 is (0.00400, 0.00600)
W = 6491.5
Test of ETA1 = ETA2 vs ETA1 > ETA2 is significant at 0.0000
The test is significant at 0.0000 (adjusted for ties)

Mann-Whitney Test and CI: CONTROL-Width, EXPERIMENTAL EVENT C-Width

| | | |
|---|---|---|
| CONTROL-Widt | N = 69 | Median = 0.01800 |
| Event C-Widt | N = 75 | Median = 0.00900 |

Point estimate for ETA1 - ETA2 is 0.00500
95.0 Percent CI for ETA1 - ETA2 is (0.00400, 0.00700)
W = 6649.0
Test of ETA1 = ETA2 vs ETA1 > ETA2 is significant at 0.0000
The test is significant at 0.0000 (adjusted for ties)

Mann-Whitney Test and CI: CONTROL-Width, EXPERIMENTAL EVENT D-Width

| | | |
|---|---|---|
| CONTROL-Widt | N = 69 | Median = 0.01800 |
| Event D-Widt | N = 5 | Median = 0.01300 |

Point estimate for ETA1 - ETA2 is 0.00500
95.2 Percent CI for ETA1 - ETA2 is (−0.00100, 0.00600)
W = 2666.0
Test of ETA1 = ETA2 vs ETA1 > ETA2 is significant at 0.0465
The test is significant at 0.0446 (adjusted for ties)

TABLE 5

Chi-square test for association (non-independence)

Results for: CONTROL vs EXPERIMENTAL EVENT B
Expected counts are printed below observed counts

| | 0.005-0.7 | 0.010-0.21 | 0.015-0.42 | Total |
|---|---|---|---|---|
| 1 | 24.14 | 20.76 | 25.10 | 70 |
| 2 | 43 | 22 | 10 | 75 |
| | 25.86 | 22.24 | 26.90 | |
| Total | 50 | 43 | 52 | 145 |

Chi-Sq = 12.168 + 0.003 + 11.373 +11.357 + 0.003 + 10.615 = 45.517
DF = 2, P-Value = 0.000

Results for: CONTROL vs EXPERIMENTAL EVENT C
Expected counts are printed below observed counts

| | 0.005-0.7 | 0.010-0.21 | 0.015-0.42 | Total |
|---|---|---|---|---|
| 1 | 22.21 | 24.62 | 23.17 | 70 |
| 2 | 39 | 30 | 6 | 75 |
| | 23.79 | 26.38 | 24.83 | |
| Total | 46 | 51 | 48 | 145 |

Chi-Sq = 10.413 + 0.532 + 15.297 +9.719 + 0.497 + 14.278 = 50.737
DF = 2, P-Value = 0.000

Results for: CONTROL vs EXPERIMENTAL EVENT D
Expected counts are printed below observed counts

| | 0.005-0.7 | 0.010-0.21 | 0.015-0.42 | Total |
|---|---|---|---|---|
| 1 | 6.53 | 24.27 | 39.20 | 70 |
| 2 | 0.47 | 1.73 | 2.80 | 5 |
| Total | 7 | 26 | 42 | 75 |

Chi-Sq = 0.033 + 0.440 + 0.200 +0.467 + 6.156 + 2.800 = 10.096
DF = 2
* WARNING * 1 cells with expected counts less than 1.0
* Chi-Square approximation probably invalid
3 cells with expected counts less than 5.0
[1 = CONTROL, 2 = Event##]

TABLE 6

Kolmogorov-Smirnov Two-Sample Tests (SAS Proc NPAR1WAY) comparing the each head capsule width distribution to the distribution for the CONTROL line A. EXPERIMENTAL EVENT B
Kolmogorov-Smirnov Test for variable HCW classified by variable Event

| Event | N | EDF at Maximum | Deviation from Mean at Maximum |
|---|---|---|---|
| Event B | 75 | 0.573333 | 1.978918 |
| CONTROL | 70 | 0.100000 | −2.048375 |
| Total | 145 | 0.344828 | |

Maximum Deviation Occurred at Observation 82
Value of HCW at Maximum = 0.0090

Kolmogorov-Smirnov Two-Sample Test (Asymptotic)

| | | | |
|---|---|---|---|
| KS | 0.236526 | D | 0.473333 |
| KSa | 2.848149 | Pr > KSa | <.0001 |

B. EXPERIMENTAL EVENT C

| Event | N | EDF at Maximum | Deviation from Mean at Maximum |
|---|---|---|---|
| Event C | 75 | 0.973333 | 2.396999 |
| CONTROL | 70 | 0.400000 | −2.481130 |
| Total | 145 | 0.696552 | |

Maximum Deviation Occurred at observation 73
Value of HCW at Maximum = 0.0160

Kolmogorov-Smirnov Two-sample Test (Asymptotic)

| | | | |
|---|---|---|---|
| KS | 0.286496 | D | 0.573333 |
| KSa | 3.449871 | Pr > KSa | <.0001 |

C. EXPERIMENTAL EVENT D

| Event | N | EDF at Maximum | Deviation from Mean at Maximum |
|---|---|---|---|
| Event D | 5 | 1.000000 | 1.401269 |
| CONTROL | 70 | 0.328571 | −0.374505 |
| Total | 75 | 0.373333 | |

Maximum Deviation occurred at observation 28
Value of HCW at Maximum = 0.0130

Kolmogorov-Smirnov Two-Sample Test (Asymptotic)

| | | | |
|---|---|---|---|
| KS | 0.167484 | D | 0.671429 |
| KSa | 1.450451 | Pr > KSa | 0.0298 |

TABLE 7

Descriptive statistics of western corn rootworm larval head capsule widths measured in ocular grid squares (width of 1 grid square = 0.079 mm) and results from the Quantile-Quantile test comparing the distributions of head capsule widths between the reference CONTROL and 2 experimental transgenic events (EXPERIMENTAL EVENTS B, and C).

A) Descriptive Statistics of Head Capsule Widths in Ocular grid squares
Analysis Variable: Widths

| Event | N Obs | N | Mean | Median | Std Dev | Std Error | Minimum | Maximum | Lower Quartile | Upper Quartile |
|---|---|---|---|---|---|---|---|---|---|---|
| B | 75 | 75 | 3.639 | 2.904 | 1.127 | 0.130 | 2.581 | 6.453 | 2.904 | 4.194 |
| C | 75 | 75 | 3.493 | 2.904 | 0.926 | 0.107 | 1.613 | 6.453 | 2.904 | 4.194 |
| Control | 69 | 69 | 5.078 | 5.808 | 1.280 | 0.154 | 2.258 | 6.453 | 3.872 | 6.130 |
| D | 5 | 5 | 4.065 | 4.194 | 0.176 | 0.079 | 3.872 | 4.194 | 3.872 | 4.194 |

B) Quantile-Quantile test for CONTROL-Width vs. EXPERIMENTAL EVENT B-Width
Pearson Correlation Coefficients, N = 100
Prob > |r| under H0: Rho = 0

|  | qx1 | qy1 |
|---|---|---|
| qx1 quantiles of Control | 1.00000 | 0.71146 <.0001 |
| qy1 quantiles of B | 0.71146 <.0001 | 1.00000 |

Pearson Correlation Statistics (Fisher's z Transformation)

| Variable | With Variable | N | Sample Correlation | Fisher's z | Bias Adjustment | Correlation Estimate | Upper 95% CL | H0: Rho >= Rho0 Rho0 | p Value |
|---|---|---|---|---|---|---|---|---|---|
| qx1 | qy1 | 100 | 0.71146 | 0.89013 | 0.00359 | 0.70968 | 0.783182 | 0.99000 | <.0001 |

C) Quantile-Quantile test for CONTROL-Width vs. EXPERIMENTAL EVENT C-Width
Pearson Correlation Coefficients, N = 100
Prob > |r| under H0: Rho = 0

|  | qx1 | qy1 |
|---|---|---|
| qx1 quantiles of Control | 1.00000 | 0.76959 <.0001 |
| qy1 quantiles of C | 0.76959 <.0001 | 1.00000 |

Pearson Correlation Statistics (Fisher's z Transformation)

| Variable | With Variable | N | Sample Correlation | Fisher's z | Bias Adjustment | Correlation Estimate | Upper 95% CL | H0: Rho >= Rho0 Rho0 | p Value |
|---|---|---|---|---|---|---|---|---|---|
| qx1 | qy1 | 100 | 0.76959 | 1.01932 | 0.00389 | 0.76800 | 0.828221 | 0.99000 | <.0001 |

D) Quantile-Quantile test for EXPERIMENTAL EVENT B-Width vs. EXPERIMENTAL EVENT C-Width
Pearson Correlation Coefficients, N = 100
Prob > |r| under H0: Rho = 0

|  | qx1 | qy1 |
|---|---|---|
| qx1 quantiles of B | 1.00000 | 0.93941 <.0001 |
| qy1 quantiles of C | 0.93941 <.0001 | 1.00000 |

Pearson Correlation Statistics (Fisher's z Transformation)

| Variable | With Variable | N | Sample Correlation | Fisher's z | Bias Adjustment | Correlation Estimate | Upper 95% CL | H0: Rho >= Rho0 Rho0 | p Value |
|---|---|---|---|---|---|---|---|---|---|
| qx1 | qy1 | 100 | 0.93941 | 1.73304 | 0.00474 | 0.93885 | 0.955834 | 0.99000 | <.0001 |

TABLE 8

Log-Rank and Wilcoxon tests for the equality of the four head capsule distributions A. Kaplan-Meier Fit of EXPERIMENTAL EVENT B vs CONTROL Test Statistics

| Method | Chi-Square | DF | P-Value |
|---|---|---|---|
| Log-Rank | 35.1543 | 1 | 0.0000 |
| Wilcoxon | 38.9217 | 1 | 0.0000 |

B. Kaplan-Meier Fit of EXPERIMENTAL EVENT C vs CONTROL Test Statistics

| Method | Chi-Square | DF | P-Value |
|---|---|---|---|
| Log-Rank | 52.2390 | 1 | 0.0000 |
| Wilcoxon | 48.1117 | 1 | 0.0000 |

C. Kaplan-Meier Fit of EXPERIMENTAL EVENT D vs CONTROL Test Statistics

| Method | Chi-Square | DF | P-Value |
|---|---|---|---|
| Log-Rank | 5.5431 | 1 | 0.0186 |
| Wilcoxon | 3.7255 | 1 | 0.0536 |

TABLE 9

Descriptive Statistics for western corn rootworm larval head capsule widths obtained from a miniaturized version of the sublethal seedling assay system.

| Variable | Event | N | Mean | Median | StDev | SE Mean |
|---|---|---|---|---|---|---|
| HW(Inches) | Control | 150 | 0.01991 | 0.02015 | 0.00089 | 0.00007 |

| Variable | Event | Minimum | Maximum | Q1 | Q3 |
|---|---|---|---|---|---|
| HW(Inches) | Control | 0.01860 | 0.02170 | 0.01860 | 0.02015 |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the inventions set forth herein will come to mind to one skilled in the art to which these inventions pertain having the benefit of the teachings presented in the foregoing descriptions and the associated drawings. For example, though examples are presented herein of various statistical treatments of the collected data, one skilled in the art will appreciate that the data may be analyzed in many different manners consistent with the parameters of the study being investigated. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of evaluating efficacy of a protection mechanism of a protected plant against an insect, comprising:
    (a) exposing a population of immature insects that belong to an insect species having a plurality of instars to a specimen of the protected plant such that the protected plant is at least contacted thereby, the exposure extending for a selected time period corresponding to a sublethal exposure of the insect population to the protected plant, said time period being set so that more than 50% of the insects do not die during the time period and so that the time period expires before 90% of the insect population leaves the larval or nymphal development stage;
    (b) halting the exposure of the insect population to the protected plant following the selected time period and collecting at least some of the immature insects;
    (c) measuring a physical characteristic of at least some of the collected immature insects; and
    (d) statistically analyzing the measured physical characteristics so as to determine efficacy of the protection mechanism of the protected plant,
    wherein said statistical analysis comprises systematically comparing a distribution of said collected insects with a corresponding distribution of collected insects of a control entity.

2. The method of claim 1, wherein said protected plant is a corn plant and wherein exposing said insect population further comprises exposing a population of corn rootworm larvae to the protected plant, wherein said corn rootworm larvae are from the genus *Diabrotica*.

3. The method of claim 1, wherein measuring a physical characteristic further comprises measuring a head capsule width of at least some of the collected immature insects.

4. The method of claim 3, further comprising estimating a proportion of instars for insects subjected to a protected plant and a proportion of instars for insects from the control entity using a statistical model, and determining an odds ratio based on the estimated proportions.

5. The method of claim 1, wherein measuring a physical characteristic comprises measuring larval body size.

6. The method of claim 5, wherein measuring larval body size comprises:
    capturing an image of the collected insects;
    processing the captured image using image analysis software to separate larvae from a background image; and
    determining body size of the separated larvae.

7. The method of claim 1, wherein statistically analyzing the measured physical characteristics in comparison to a selected control entity further comprises statistically analyzing the measured physical characteristics in comparison to a selected control entity comprising at least one of:
    (a) immature insects of the insect species exposed to a different specimen of the protected plant having the protection mechanism;
    (b) immature insects of the insect species exposed to a non-protected plant;
    (c) immature insects of a different insect species exposed to the protected plant; (d) immature insects of the insect species exposed to the protected plant having a selected dosage of the trait;
    (e) immature insects of the insect species exposed to a selected specimen of the protected plant;
    (f) immature insects of the insect species exposed to the protected plant having a selected protection mechanism;

(g) immature insects of the insect species exposed for a lesser duration to the protected plant having the protection mechanism; and (h) immature insects of the insect species exposed to the protected plant having the protection mechanism and a selected plant characteristic.

8. The method of claim 1, wherein statistically analyzing the measured physical characteristics further comprises statistically analyzing a total amount of the collected immature insects and a distribution of the measured physical characteristics so as to determine efficacy of the protection mechanism of the protected plant.

9. The method of claim 1, wherein statistically analyzing the measured physical characteristics further comprises statistically analyzing the measured physical characteristics so as to evaluate at least one of:

(a) a difference in efficacy between protection mechanisms;

(b) a difference in efficacy between at least two specimens of the protected plant each prepared with the protection mechanism;

(c) a difference in efficacy where protection mechanisms are stacked;

(d) a difference in efficacy of the protection mechanism of the protected plant between at least two insect species;

(e) a difference in efficacy of the protection mechanism of the protected plant for at least two insect species between at least two specimens of the protected plant each prepared with the protection mechanism;

(f) a difference in efficacy of the protection mechanism between different dosages thereof; and (g) a resistance to the protection mechanism.

10. A method of evaluating efficacy of a protection mechanism of a protected plant against an insect, comprising:

(a) exposing a first and a second population of immature insects to the protected plant such that the protected plant is at least contacted thereby, wherein the immature insects that belonging to an insect species having a plurality of instars and wherein the exposure extends for a selected time period corresponding to a sublethal exposure of each immature insect population to the protected plant, said time period being set so that more than 50% of the insects do not die during the time period and so that the time period expires before 90% of each insect population leaves the larval or nymphal development stage;

(b) halting the exposure of both immature insect populations to the protected plant following the selected time period and collecting the immature insects of each population;

(c) measuring a physical characteristic of at least some of the collected insects of each of the first and second insect larval populations;

(d) statistically analyzing the measured physical characteristics for the insects of each of the first and second insect populations; and (e) comparing the statistically analyzed measured physical characteristics of the first insect population to the statistically analyzed measured physical characteristics of the second insect population so as to determine a difference in efficacy of the protection mechanism of the protected plant between the insect larval populations, wherein said statistical analysis comprises systematically comparing a distribution of said collected insects of said first insect population with a corresponding distribution of collected insects of said second insect population.

11. The method of claim 10, wherein the first insect population is exposed to a first specimen of the protected plant having the protection mechanism and the second insect population is exposed to a second specimen of the protected plant having the protection mechanism so as to determine a difference in efficacy between specimens of the protected plant.

12. The method of claim 10, wherein statistically analyzing the measured physical characteristics further comprises statistically analyzing the measured physical characteristics for each of the first and second insect larval populations in comparison to a single selected control entity, prior to comparing the statistically analyzed measured physical characteristics of the first insect population to the statistically analyzed measured physical characteristics of the second insect population.

13. A method of evaluating efficacy of a protection mechanism of a protected plant against an insect, comprising:

(a) exposing a first population of an immature insect to a first specimen of the protected plant having a protection mechanism and a second population of the immature insect to a second specimen of the protected plant also having the protection mechanism, the immature insect that belong to an insect species having a plurality of instars and the first and second populations being exposed to first and second specimens of the protected plant such that the respective specimen is at least contacted thereby, the exposure extending for a selected time period corresponding to a sublethal exposure of each immature insect population to the respective specimen of the protected plant, said time period being set so that more than 50% of the insects do not die during the time period and so that the time period expires before 90% of each insect population leaves the larval or nymphal development stage;

(b) halting the exposure of both immature insect populations to the respective specimen of the protected plant following the selected time period and collecting immature insects of each population;

(c) measuring a physical characteristic of at least some of the collected immature insects of each of the first and second insect populations;

(d) statistically analyzing the measured physical characteristics for the collected immature insects of each of the first and second insect populations; and (e) comparing the statistically analyzed measured physical characteristics of the first immature insect population to the statistically analyzed measured physical characteristics of the second immature insect population so as to determine a difference in efficacy of the protection mechanism between the specimens of the protected plant, wherein said statistical analysis comprises systematically comparing a distribution of said collected insects of said first insect population with a corresponding distribution of collected insects of said second insect population.

14. A method of evaluating efficacy of a protection mechanism of a protected plant against an insect, comprising:

(a) exposing a first population of an immature insect to a first sample of the protected plant having a first dosage of a protection mechanism and a second population of the immature insect to a second sample of the protected plant having a second dosage of the protection mechanism, the first dosage being different from the second dosage and the immature insect that belong to an insect species having a plurality of instars, the first and second populations being exposed to first and second samples of the protected plant such that the respective sample is at least contacted thereby, the exposure extending for a selected time period corresponding to a sublethal exposure of each insect population to the respective sample of the protected plant, said time period being set so that more than 50% of the insects do not die during the time period and so that the time period expires before 90% of each insect population leaves the larval or nymphal development stage;

(b) halting the exposure of both insect populations to the respective sample of the protected plant following the selected time period and collecting the insects of each population;

(c) measuring a physical characteristic of at least some collected insects of each of the first and second insect populations;

(d) statistically analyzing the measured physical characteristics for the collected insects of each of the first and second insect populations; and (e) comparing the statistically analyzed measured physical characteristics of the first insect population to the statistically analyzed measured physical characteristics of the second insect population so as to determine a difference in efficacy between the dosages of the protection mechanism of the protected plant, wherein said statistical analysis comprises systematically comparing a distribution of said collected insects of said first insect population with a corresponding distribution of collected insects of said second insect population.

15. A method of evaluating efficacies of protection mechanisms of a first protected plant and a second protected plant against an insect, comprising:

(a) exposing a first population of an immature insect to a sample of a first protected plant having a first protection mechanism and exposing a second population of the insect to a sample of a second protected plant having a second protection mechanism, wherein said first protection mechanism is different from said second protection mechanism and wherein said immature insect belongs to an insect species having a plurality of instars, wherein said first and second populations are exposed to said samples of said first and second protected plants, respectively, such that the respective sample is at least contacted thereby, the exposure extending for a selected time period corresponding to a sublethal exposure of each insect population to the respective sample of the protected plant, said time period being set so that more than 50% of the insects do not die during the time period and so that the time period expires before 90% of each insect population leaves the larval or nymphal development stage;

(b) halting the exposure of both insect populations to the respective sample of the protected plant following the selected time period and collecting the insects of each population;

(c) measuring a physical characteristic of at least some collected insects of each of the first and second insect populations;

(d) statistically analyzing the measured physical characteristics for the collected insects of each of the first and second insect populations; and (e) comparing the statistically analyzed measured physical characteristics of the first insect population to the statistically analyzed measured physical characteristics of the second insect population so as to determine a difference in efficacy between the first and second protection mechanisms of the protected plant, wherein said statistical analysis comprises systematically comparing a distribution of said collected insects of said first insect population with a corresponding distribution of collected insects of said second insect population.

16. A method of evaluating efficacies of protection mechanisms of a first protected plant, a second protected plant, and a third protected plant against an insect, comprising:

(a) exposing a first population of an immature insect to a first sample of the protected plant having a first protection mechanism, a second population of the immature insect to a second sample of the protected plant having a second protection mechanism, and a third population of the immature insect to a third sample of the protected plant having both of said first and second protection mechanisms, wherein said first protection mechanism is different from said second protection mechanism and said insect population is of an insect species having a plurality of instars, wherein said first, second, and third populations are exposed to said samples of said first, second, and third protected plant, respectively, such that the respective sample is at least contacted thereby, wherein the exposure extends for a selected time period that corresponds to a sublethal exposure of each insect population to the respective sample of the protected plant, said time period being set so that more than 50% of the insects do not die during the time period and so that the time period expires before 90% of each insect population leaves the larval or nymphal development stage;

(b) halting the exposure of each insect population to the respective sample of the protected plant following the selected time period and collecting at least some insects of each population;

(c) measuring a physical characteristic of at least some collected insects of each of the first, second, and third insect populations;

(d) statistically analyzing the measured physical characteristics for insects of each of the first, second, and third insect populations; and (e) comparing the statistically analyzed measured physical characteristics of the third insect population to each of the statistically analyzed measured physical characteristics of the first and second insect populations so as to determine the effect of stacking the first protection mechanism and the second protection mechanism on the efficacies of the protection mechanisms, wherein said statistical analysis comprises systematically comparing distributions of said collected insects of said first, second, and third insect populations.

17. A method of evaluating efficacy of a protection mechanism of a protected plant having a protection mechanism against an insect, comprising:

(a) exposing a population of a first immature insect and a population of a second immature insect to the protected plant such that the protected plant is at least contacted thereby, wherein the first immature insect belongs to a species having a plurality of instars and the second immature insect belongs to a different species having a plurality of instars, wherein the exposure extends for a selected time period corresponding to a sublethal exposure of each population to the protected plant, said time period being set so that more than 50% of the insects do not die during the time period and so that the time period expires before 90% of each insect population leaves the larval or nymphal development stage;

(b) halting the exposure of both populations to the protected plant following the selected time period and collecting at least some insects of each population;

(c) measuring a physical characteristic of at least some of the collected insects of each population;

(d) statistically analyzing the measured physical characteristics; and (e) comparing the statistically analyzed measured physical characteristics of the population of the first immature insect to the statistically analyzed measured physical characteristics of the population of the second immature insect so as to determine a difference in efficacy of the protection mechanism of the protected plant between the first and second immature insect, wherein said statistical analysis comprises systematically comparing a distribution of said collected insects of said first insect population with a corresponding distribution of collected insects of said second insect population.

18. A method of evaluating efficacy of a protection mechanism of a protected plant, against an insect, comprising:

(a) exposing a population of a first immature insect to a first specimen of the protected plant having a protection mechanism and a population of a second immature insect to a second specimen of the protected plant also having the protection mechanism, each immature insect belonging to an insect species having a plurality of instars and the first immature insect belonging to a different insect species than the second immature insect, the populations of the first and second immature insect being exposed to the respective specimen of the protected plant such that the respective specimen is at least contacted thereby, the exposure extending for a selected time period corresponding to a sublethal exposure of each population of immature insect to the respective specimen of the protected plant, said time period being set so that more than 50% of the insects do not die during the time period and so that the time period expires before 90% of each insect population leaves the larval or nymphal development stage;

(b) halting the exposure of both populations of immature insect to the respective specimen of the protected plant following the selected time period and collecting at least some immature insects of each population;

(c) measuring a physical characteristic of at least some collected immature insects of each of the populations of the immature insect;

(d) statistically analyzing the measured physical characteristics; and (e) comparing the statistically analyzed measured physical characteristics of the population of the first immature insect to the statistically analyzed measured physical characteristics of the population of the second immature insect so as to determine a difference in efficacy of the protection mechanism of the protected plant between the first and second immature insect and between the specimens of the protected plant, wherein said statistical analysis comprises systematically comparing a distribution of said collected insects of said first insect population with a corresponding distribution of collected insects of said second insect population.

19. A method of evaluating an insect population with respect to an effect thereon of a protected plant having a protection mechanism, comprising:

(a) exposing a first generation population of immature insect belonging to a species having a plurality of instars to the protected plant such that the protected plant is at least contacted thereby, the exposure extending for a first selected time period, and collecting at least some of the immature insects, said first selected time period being set so that more than 50% of the insects of the first generation population do not die during the time period and so that the time period expires before 90% of the first generation population leaves the larval or nymphal development stage;

(b) measuring a physical characteristic of at least some of the collected insects of the first generation population;

(c) statistically analyzing the measured physical characteristics so as to determine efficacy of the protection mechanism of the protected plant with respect to the first generation population of immature insect;

(d) allowing the first generation population of immature insects to develop into adult insect and then intermating adult insects within the adult insect population so as to form a second generation population of immature insects;

(e) exposing the second generation population of immature insects to the protected plant such that the protected plant is at least contacted thereby, the exposure extending for a second selected time period, and collecting at least some immature insects following the second selected time period, said second selected time period being set so that more than 50% of the insects of the second generation population do not die during the time period and so that the time period expires before 90% of the second generation population leaves the larval or nymphal development stage;

(f) measuring a physical characteristic of at least some collected immature insects in the second generation population;

(g) statistically analyzing the measured physical characteristics for at least some of the collected insects so as to determine efficacy of the protection mechanism of the protected plant with respect to the second generation population of immature insects; and (h) comparing the statistically analyzed measured physical characteristics of the second generation population of immature insects to the statistically analyzed measured physical characteristics of the first generation population of immature insects so as to determine a change in susceptibility of the insects to the protection mechanism of the protected plant between the first and second generation populations, wherein said statistical analysis comprises systematically comparing a distribution of said collected insects of said first generation population with a corresponding distribution of collected insects of said second generation population.

20. A method of evaluating an insect population with respect to an effect thereon of a protected plant having a protection mechanism, comprising:

(a) exposing a field population of immature insect belong to an insect species having a plurality of instars to the protected plant such that the protected plant is at least contacted thereby, the exposure extending for a first selected time period, said first selected time period being set so that more than 50% of the insects do not die during the time period and so that the time period expires before 90% of the field population leaves the larval or nymphal development stage;

(b) collecting a first sample portion of the field population of immature insect following the first selected time period;

(c) measuring a physical characteristic of immature insects in the first sample portion;

(d) statistically analyzing the measured physical characteristics so as to determine efficacy of the protection mechanism of the protected plant with respect to the first sample portion of insects;
(e) collecting a second sample portion of the field population of insects following a second selected time period, the second selected time period being greater than the first selected time period;
(f) measuring a physical characteristic of each insect in the second sample portion;
(g) statistically analyzing the measured physical characteristics so as to determine efficacy of the protection mechanism of the protected plant with respect to the second sample portion of insects; and
(h) comparing the statistically analyzed measured physical characteristics of the second sample portion of insects to the statistically analyzed measured physical characteristics of the first sample portion of insects so as to determine a change in susceptibility of the insects to the protection mechanism of the protected plant between the first and second sample portions in relation to the respective selected time period,
wherein said statistical analysis comprises systematically comparing a distribution of said collected insects of said first sample portion with a corresponding distribution of collected insects of said second sample portion.

\* \* \* \* \*